United States Patent

Kilama et al.

Patent Number: 5,719,104
Date of Patent: Feb. 17, 1998

[54] HERBICIDAL BICYCLIC AND TRICYCLIC IMIDES

[75] Inventors: John J. Kilama, Wilmington, Del.; Karlheinz Drauz, Freigericht, Germany; Wonpyo Hong, Hockessin, Del.; Matthias Schäfer, Goldbach, Germany

[73] Assignee: E. I. du Pont de Nemours and Company, Wilmington, Del.

[21] Appl. No.: 718,337

[22] PCT Filed: Apr. 6, 1995

[86] PCT No.: PCT/US95/03932

§ 371 Date: Oct. 3, 1996

§ 102(e) Date: Oct. 3, 1996

[87] PCT Pub. No.: WO95/27698

PCT Pub. Date: Oct. 19, 1995

Related U.S. Application Data

[63] Continuation-in-part of Ser. No. 224,934, Apr. 8, 1994, abandoned.

[51] Int. Cl.$^6$ ............... C07D 487/02; A01N 43/56
[52] U.S. Cl. ............... 504/236; 504/221; 504/225; 504/261; 504/280; 504/285; 504/286; 544/82; 544/105; 544/236; 548/262.4; 548/453; 548/454; 548/513
[58] Field of Search ............... 544/236, 105, 544/82; 504/236, 261, 280, 286, 285, 221, 225; 548/262.4, 453, 454, 513

[56] References Cited

U.S. PATENT DOCUMENTS

| | | | |
|---|---|---|---|
| 4,680,412 | 7/1987 | Hamprecht et al. | 548/480 |
| 4,839,378 | 6/1989 | Koyama et al. | 514/417 |
| 4,881,967 | 11/1989 | Semple | 71/92 |
| 4,933,166 | 6/1990 | Shen et al. | 424/10 |
| 5,034,051 | 7/1991 | Kume et al. | 71/92 |
| 5,047,553 | 9/1991 | Nowak et al. | 548/476 |
| 5,102,447 | 4/1992 | Gates | 71/95 |
| 5,133,799 | 7/1992 | Seele et al. | 71/92 |
| 5,190,573 | 3/1993 | Misslitz et al. | 504/292 |
| 5,276,009 | 1/1994 | Muenster et al. | 504/284 |

FOREIGN PATENT DOCUMENTS

| | | |
|---|---|---|
| 0 075 267 | 3/1983 | European Pat. Off. |
| 0 104 484 | 4/1984 | European Pat. Off. |
| 0 176 101 | 4/1986 | European Pat. Off. |
| 0 211 805 | 2/1987 | European Pat. Off. |
| 0 230 874 | 8/1987 | European Pat. Off. |
| 0 312 763 | 4/1989 | European Pat. Off. |
| 0 385 231 | 9/1990 | European Pat. Off. |
| 0 400 427 | 12/1990 | European Pat. Off. |
| 0 456 108 | 11/1991 | European Pat. Off. |
| 0 493 721 | 7/1992 | European Pat. Off. |
| 0 493 606 | 7/1992 | European Pat. Off. |
| 50-142730 | 11/1975 | Japan |
| 36-3278 | 3/1991 | Japan |
| 32-1032 | 3/1991 | Japan |
| 31-69859 | 7/1991 | Japan |
| 32-84678 | 12/1991 | Japan |
| 41-39168 | 5/1992 | Japan |
| 41-39169 | 5/1992 | Japan |
| WO 92/09575 | 6/1992 | WIPO |

*Primary Examiner*—Joseph Mckane

[57] ABSTRACT

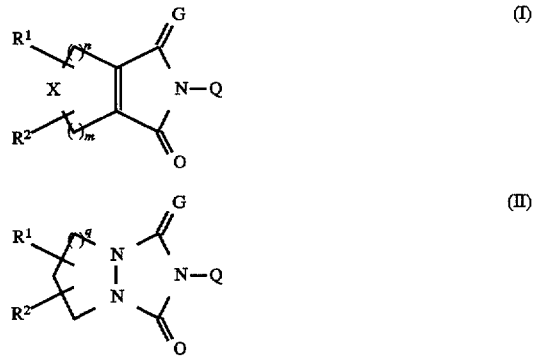

Bicyclic imides of formulae (I) and (II) and their agriculturally-suitable salts, are disclosed which are useful for controlling undesirable vegatation, wherein G is O or S; n and m are each independently 0; 1; 2; or 3; provided that m+n is 2 or 3; q is 1 or 2; X is $CH_2$; CH(halogen); $CF_2$; $CHOCH_2F$; $CHOCF_3$; $CHOCH_2CF_3$; O; $S(O)_{0-2}$; NH; $N(C_1-C_4$ alkyl); or $N(C_1-C_4$ haloalkyl); and $R^1$, $R^2$, and Q are as defined in the disclosure. Also disclosed are compositions containing the bicyclic imides of formulae (I) and (II) and a method for controlling growth of undesired vegetation comprising applying to the locus to be protected an effective amount, of the bicyclic imides formulae (I) and (II).

9 Claims, No Drawings

HERBICIDAL BICYCLIC AND TRICYCLIC IMIDES

This application of a 371 of PCT/US 95/03932 filed Apr. 6, 1995 and a CIP of Ser. No. 08/224,934 filed Apr. 8, 1994 now abandoned.

This invention comprises certain bicyclic imides, their agriculturally-suitable salts and compositions, and methods of their use for weed control in crops.

WO 909575 (BASF) discloses compounds of formula i

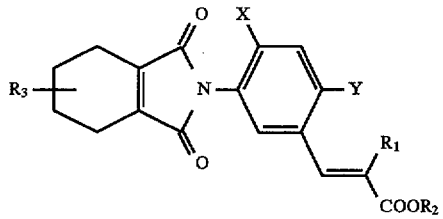

wherein $R_1$=halogen, $R_2$=alkyl, etc., $R_3$=H or $CH_3$, X =H or halogen, and Y=halogen. The compounds of the present invention differ from those disclosed in this reference in that a non-hydrogen, non-alkyl substituent is present on the cyclohexene ring moiety.

JP 3,063,278 (Nissan) discloses compounds of Formula ii

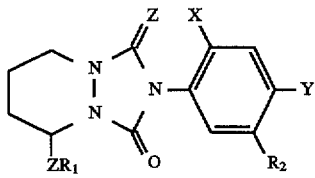

wherein Z is O or S, and $R_1$ is H, alkyl, haloalkyl, etc. The N-phenyl tetrahydrotriazolopyridazines of the present invention differ from the compounds disclosed in JP 3,063,278 in the nature of the substitution on the tetrahydropyridazine ring.

U.S. Pat. Nos. 4,881,967, 5,077,401, and 5,108,483 also disclose related tetrahydrotriazolopyridazines. The compounds of the present invention also differ from the compounds disclosed in these references in the nature of the substitution on the tetrahydropyridazine ring.

SUMMARY OF THE INVENTION

This invention pertains to compounds of Formulae I and II, or an agriculturally-suitable salt thereof, for controlling undesirable vegetation:

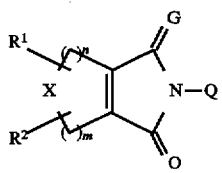

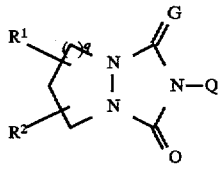

wherein

G is O; S; NH; $N(C_1-C_4$ alkyl); or $N(C_1-C_4$ haloalkyl);

$R^1$ is hydrogen; halogen; hydroxy; SH; $C_1-C_3$ alkoxy; $C_1-C_3$ haloalkoxy; $C_1-C_3$ alkylthio; $C_1-C_3$ haloalkylthio; $C_2-C_4$ alkylcarbonyloxy; or $C_2-C_4$ haloalkylcarbonyloxy;

$R^2$ is hydrogen; hydroxy; or halogen; or when $R^1$ and $R^2$ are bonded to the same carbon atom they can be taken together with the carbon to which they are attached to form C=O; or when $R^1$ and $R^2$ are bonded to adjacent atoms they can be taken together with the carbons to which they are attached to form

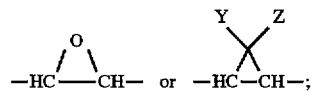

Y and Z are each independently H; halogen; $C_1-C_2$ alkyl; or $C_1-C_2$ haloalkyl;

n and m are each independently 0; 1; 2; or 3; provided that m+n is 2 or 3;

q is 1 or 2;

X is $CH_2$; CH(halogen); $CF_2$; $CHOCH_2F$; $CHOCF_3$; $CHOCH_2CF_3$; O; $S(O)_{0-2}$; NH; $N(C_1-C_4$ alkyl); or $N(C_1-C_4$ haloalkyl);

Q is selected from the group

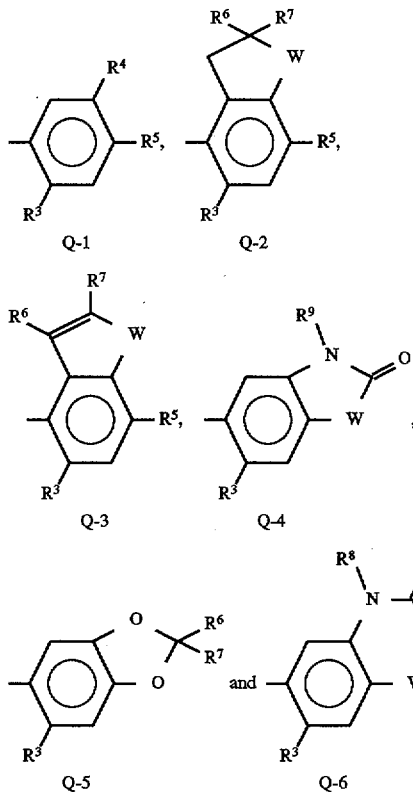

W is O or S;

$R^3$ is chlorine or fluorine;

$R^4$ is H; $C_1-C_8$ alkyl; $C_1-C_8$ haloalkyl; halogen; OH; $OR^9$; SH; $S(O)_pR^9$; $COR^9$; $CO_2R^9$; $C(O)SR^9$; $C(O)NR^{11}R^{12}$; CHO; $CR^{11}$=$NOR^{18}$; CH=$CR^{19}CO_2R^9$; $CH_2CHR^{19}CO_2R^9$; $CO_2N$=$CR^{13}R^{14}$; $NO_2$; CN; $NHSO_2R^{15}$; $NHSO_2NHR^{15}$; $NR^9R^{20}$; $NH_2$ or phenyl optionally substituted with at least one member independently selected from $C_1-C_4$ alkyl;

p is 0; 1; or 2;

$R^5$ is $C_1-C_2$ alkyl; $C_1-C_2$ haloalkyl; $OCH_3$; $SCH_3$; $OCHF_2$; halogen; CN or $NO_2$;

$R^6$ is H; $C_1$–$C_3$ alkyl; $C_1$–$C_3$ haloalkyl; or halogen;

$R^7$ is H; $C_1$–$C_3$ alkyl; halogen; $C_1$–$C_3$ haloalkyl; cyclopropyl; vinyl; $C_2$ alkynyl; CN; $C(O)R_{20}$; $CO_{20}R^{20}$; $C(O)NR^{20}R^{21}$; $CR^{16}R^{17}CN$; $CR^{16}R^{17}C(O)R^{20}$; $CR^{16}R^{17}CO_2R^{20}$; $CR^{16}R^{17}C(O)NR^{20}R^{21}$; $CHR^{16}OH$; $CHR^{16}OC(O)R^{20}$; $OCHR^{16}OC(O)NR^{20}R^{21}$; or Q is Q-2 and $R^6$ and $R^7$ are taken together with the carbon to which they are attached to form C=O;

$R^8$ is $C_1$–$C_6$ alkyl; $C_1$–$C_6$ haloalkyl; $C_2$–$C_6$ alkoxyalkyl; $C_3$–$C_6$ alkenyl; or $C_3$–$C_6$ alkynyl;

$R^9$ is $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_1$–$C_8$ alkylsulfonyl; phenylsulfonyl optionally substituted on the phenyl ring with at least one substituent selected from the group halogen and $C_1$–$C_4$ alkyl; $C_4$–$C_8$ alkoxyalkoxyalkyl; $C_4$–$C_8$ cycloalkylalkyl; $C_4$–$C_8$ alkenoxyalkyl; $C_4$–$C_8$ alkynoxyalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; $C_4$–$C_8$ haloalkenoxyalkyl; $C_4$–$C_8$ haloalkynoxyalkyl; $C_6$–$C_8$ cycloalkylthioalkyl; $C_4$–$C_8$ alkenylthioalkyl; $C_4$–$C_8$ alkynylthioalkyl; $C_1$–$C_4$ alkyl substituted with phenoxy or benzyloxy, each ring optionally substituted with at least one substituent selected from the group halogen, $C_1$–$C_3$ alkyl and $C_1$–$C_3$ haloalkyl; $C_4$–$C_8$ trialkylsilylalkyl; $C_3$–$C_8$ cyanoakyl; $C_3$–$C_8$ halocycloalkyl; $C_3$–$C_8$ haloalkenyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $C_2$–$C_8$ alkylcarbonyl; benzyl optionally substituted with at least one substituent selected from the group halogen, $C_1$–$C_3$ alkyl and $C_1$–$C_3$ haloalkyl; $CHR^{16}COR^{10}$; $CHR^{16}CO_2R^{10}$; $CHR^{16}P(O)(OR^{10})_2$; $CHR^{16}P(S)(OR^{10})_2$; $CHR^{16}C(O)NR^{11}R^{12}$; or $CHR^{16}C(O)NH_2$;

$R^{10}$ is $C_1$–$C_6$ alkyl; $C_2$–$C_6$ alkenyl; or $C_2$–$C_6$ alkynyl; $R^{11}$ and $R^{13}$ are independently hydrogen or $C_1$–$C_4$ alkyl;

$R^{12}$ and $R^{14}$ are independently $C_1$–$C_4$ alkyl or phenyl optionally substituted with at least one substituent selected from the group halogen, $C_1$–$C_3$ alkyl and $C_1$–$C_3$ haloalkyl; or $R^{11}$ and $R^{12}$ can be taken together to form —$(CH_2)_5$—, —$(CH_2)_4$— or —$CH_2CH_2OCH_2CH_2$—, each ring thus formed optionally substituted with a substituent selected from the group $C_1$–$C_3$ alkyl, phenyl and benzyl; or $R^{13}$ and $R^{14}$ can be taken together with the carbon to which they are attached to form $C_3$–$C_8$ cycloalkyl;

$R^{15}$ is $C_1$–$C_4$ alkyl or $C_1$–$C_4$ haloalkyl;

$R^{16}$ and $R^{17}$ are independently H or $C_1$–$C_4$ alkyl;

$R^{18}$ is H; $C_1$–$C_6$ alkyl; $C_3$–$C_6$ alkenyl; or $C_3$–$C_6$ alkynyl;

$R^{19}$ is H; $C_1$–$C_4$ alkyl; or halogen;

$R^{20}$ is H; $C_1$–$C_6$ alkyl; $C_3$–$C_6$ cycloalkyl; $C_3$–$C_6$ alkenyl; $C_3$–$C_6$ alkynyl; $C_2$–$C_6$ alkoxyalkyl; $C_1$–$C_6$ haloalkyl; phenyl optionally substituted with at least one substituent selected from the group halogen, $C_1$–$C_4$ alkyl, and $C_1$–$C_4$ alkoxy; —$CH_2CO_2(C_1$–$C_4$ alkyl); or —$CH(CH_3)CO_2(C_1$–$C_4$ alkyl)$; and $R^{21}$ is H; $C_1$–$C_2$ alkyl; or $C(O)O(C_1C_4$ alkyl); provided that (i) $R^1$ is other than hydrogen in compounds of Formula I when X is $CH_2$ and $R^2$ is hydrogen; and (ii) $R^2$ is other than hydrogen or hydroxy in compounds of Formula II when Q is Q-1, Q-2, Q-4, or Q-6 and q is 2.

For reasons such as ease of synthesis and/or greater herbicidal efficacy, preferred compounds are:

Preferred 1: Compounds of Formulae I and II, and agriculturally-suitable salts thereof, wherein:

G is O;

$R^1$ is hydrogen or halogen;

$R^2$ is halogen;

Q is Q-1, Q-2 or Q-6;

$R^5$ is $C_1$–$C_2$ haloalkyl; $OCH_3$; $OCHF_2$; CN; $NO_2$; or halogen;

$R^6$ is hydrogen; $C_1$–$C_3$ alkyl; $C_2$–$C_3$ alkynyl; $C_2$–$C_3$ haloalkynyl; or halogen;

$R^7$ is H; and

W is O.

Preferred 2: Compounds of Preferred 1 wherein:

$R^4$ is halogen; $OR^9$; $SR^9$; $COR^9$; $CO_2R^9$; $C(O)NR^{11}R^{12}$; $CH=CHCO_2R^9$; $NHSO_2R^{15}$ or $NHSO_2NHR^{15}$;

$R^5$ is halogen;

$R^6$ is hydrogen or $C_1$–$C_3$ alkyl; and $R^9$ is $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_1$–$C_4$ alkyl substituted with phenoxy or benzyloxy, each ring optionally substituted with at least one substituent selected from the group halogen, $C_1$–$C_3$ alkyl and $C_1$–$C_3$ haloalkyl; $C_3$–$C_8$ haloalkenyl; $C_3$–$C_8$ haloalkynyl; $C_2$–$C_8$ alkyl carbonyl; benzyl optionally substituted with at least one substituent selected from the group halogen, $C_1$–$C_3$ alkyl and $C_1$–$C_3$ haloalkyl; $CHR^{16}COR^{10}$; $CHR^{16}CO_2R^{10}$; $CHR^{16}P(O)(OR^{10})_2$; $CHR^{16}C(O)NR^{11R}R^{12}$; or $CHR^{16}C(O)NH_2$.

Preferred 3: Compounds of Preferred 2 wherein:

$R^1$ is hydrogen or fluorine;

$R^2$ is fluorine;

X is $CH_2$ or 0;

$R^5$ is chlorine or fluorine;

$R^9$ is $C_1$–$C_6$ alkyl; $C_3$–$C_6$ alkenyl; $C_3$–$C_6$ alkynyl; $C_1$–$C_6$ haloalkyl; $C_2$–$C_8$ alkoxyalkyl; $CH_2$ substituted with phenoxy or benzyloxy, each ring optionally substituted with at least one substituent selected from the group halogen, $C_1$–$C_3$ alkyl and $C_1$–$C_3$ haloalkyl; $C_3$–$C_8$ haloalkenyl; $C_2$–$C_8$ alkylcarbonyl; benzyl optionally substituted with at least one substituent selected from the group halogen, $C_1$–$C_3$ alkyl and $C_1$–$C_3$ haloalkyl; $CHR^{16}COR^{10}$; $CHR^{16}CO_2R^{10}$; or $CHR^{16}P(O)(OR^{10})_2$.

Most preferred are compounds of Preferred 3 selected from the group:

2-[4-chloro-2-fluoro-5-(2-propynyloxy)phenyl]-6-fluorotetrahydro-1H-[1,2,4]triazolo[1,2-α]pyridazine-1,3(2H)-dione;

2-[4-chloro-2-fluoro-5-(2-propynyloxy)phenyl]-6-fluorodihydro-1H, 5H-pyrazolo[1,2-α]triazole-1,3(2H)-dione;

2-[4-chloro-2-fluoro-5-(2-propynyloxy)phenyl]-5-fluoro-4,5,6,7-tetrahydro-1H-isoindole-,1,3(2H)-dione; and 2-[4-chloro-2-fluoro-5-(2-propynyloxy)phenyl]-6,7-dihydropyrano[3,4-c]-pyrrole-1,3(2H,4H)-dione.

Another embodiment of the invention is an agriculturally suitable composition for controlling the growth of undesired vegetation comprising an effective amount of a compound of Formulae I or II, or an agriculturally-suitable salt thereof, with the substituents as defined above.

A further embodiment of the invention is a method for controlling the growth of undesired vegetation which comprises applying to the locus to be protected an effective amount of a compound of Formula I or II, or an agriculturally-suitable salt thereof, with the substituents as defined above.

Further embodiments of the invention are agriculturally suitable compositions and methods for selectively controlling undesired vegetation in the presence of desired crops, especially plantation crops, such as sugarcane, citrus, gapes, coffee, oil palm, cocoa, fruit trees, nut trees, banana, plantain, rubber, pineapple and loblolly pine.

DETAILS OF THE INVENTION

Compounds of Formulae I and II may exist as one or more stereoisomers. The various stereoisomers include enantiomers, diastereomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate and/or to selectively prepare said stereoisomers. Accordingly, the present invention comprises mixtures, individual stereoisomers, and optically active mixtures of compounds of Formula I as well as agriculturally suitable salts thereof.

The salts of the compounds of the invention include acid-addition salts with inorganic or organic acids such as hydrochloric, nitric, sulfufic, acetic, oxalic, or 4-toluenesulfonic acids. The salts of the compounds of the invention also include those formed which are organic based (e.g., pyridine, ammonia, or triethylamine) or inorganic based (e.g., sodium, potassium, lithium, calcium, magnesium or barium).

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched genes such as 1-propenyl, 2-propenyl, and the different butenyl, pentenyl and hexenyl isomers. "Alkenyl" also includes polyenes such as 1,3-hexadiene and 2,4,6-heptatriene. "Alkynyl" includes straight-chain or branched alkynes such as ethynyl, 1-propynyl, 3-propynyl and the different butynyl, pentynyl and hexynyl isomers. "Alkynyl" can also include mole ties comprised of multiple triple bonds such as 2,7-octadiyne. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkenyloxy" includes straight-chain or branched alkenyloxy moieties. Examples of alkenyloxy include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfmyl" includes both enantiomers of an alkylsulfinyl group. For example, $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Cycloalkyl" includes, for example, cyclopropyl, cyclobutyl, cyclopentyl, and cyclohexyl. The term "cycloalkoxy" includes the same groups linked through an oxygen atom such as cyclopentyloxy and cyclohexyloxy. Examples of "cycloalkylalkyl" include cyclopropylmethyl, cyclohexylethyl, and other cycloalkyl moieties bonded to straight-chain or branched alkyl groups.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $CF_2HCH_2CH_2O$ and $CF_3CH_2O$. Examples of "haloalkylthio" include $CCl_3S$, $CF_3S$, $CCl_3CH_2S$ and $CH_2ClCH_2CH_2S$.

The total number of carbon atoms in a substituent group is indicated by the "$C_i$-$C_j$" prefix where i and j are numbers from 1 to 8. For example, $C_1$-$C_3$ alkylsulfonyl designates methylsulfonyl through propylsulfonyl; $C_2$ alkoxyalkoxy designates $CH_3OCH_2O$; $C_3$ alkoxyalkoxy designates, for example, $CH_3OCH_2CH_2O$ or $CH_3CH_2OCH_2O$; and $C_4$ alkoxyalkoxy designates the various isomers of an alkoxy group substituted with a second alkoxy group containing a total of four carbon atoms, examples including $CH_3CH_2CH_2OCH_2O$, and $CH_3CH_2OCH_2CH_2O$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy-, pentoxy- or hexyloxycarbonyl isomers.

The compounds represented by Formulae I and II can be prepared by one or more of the following methods, or variations obvious to one skilled in the art, as described below in Schemes 1–20. The definitions of G, Q, X, W, n, m, p, q and $R^1$ through $R^{21}$ in the compounds of Formula 1–21 below are as defined above in the Summary of the Invention. Compounds of Formulae Ia–Ip and Formulae IIa–IIh are within the definition of compounds of Formulae I and II, respectively.

One skilled in the art will recognize that when G is O, some compounds of Formulae I and II have a plane of symmetry. Therefore, the two formulae below are equivalent.

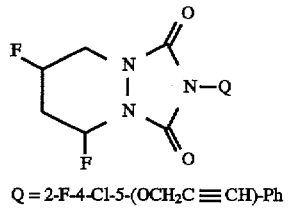

Q = 2-F-4-Cl-5-(OCH$_2$C$\equiv$CH)-Ph

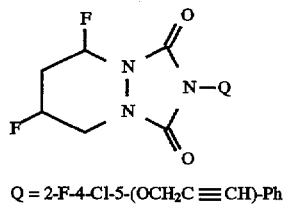

Q = 2-F-4-Cl-5-(OCH$_2$C$\equiv$CH)-Ph

Synthesis of Compounds of Formula I

Condensation of an $R^2$-substituted 1,4-cyclohexadiene 1,2-dicarboxylic arthydride with aniline in acetic acid (AcOH) at a temperature between room temperature and reflux, gives the dihydrophthalimide of Formula I, as illustrated in Scheme 1.

Scheme 1

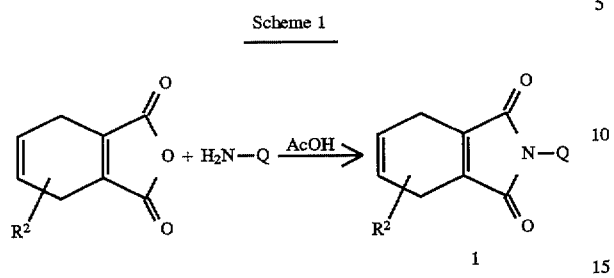

Treatment of the olefin of Formula 1 with borane in an inert solvent such as tetrahydrofuran at a temperature between about −78° C. and room temperature followed by addition of aqueous sodium hydroxide and aqueous hydrogen peroxide (preferably 30%) gives the alcohol of Formula Ia, as illustrated in Scheme 2.

Scheme 2

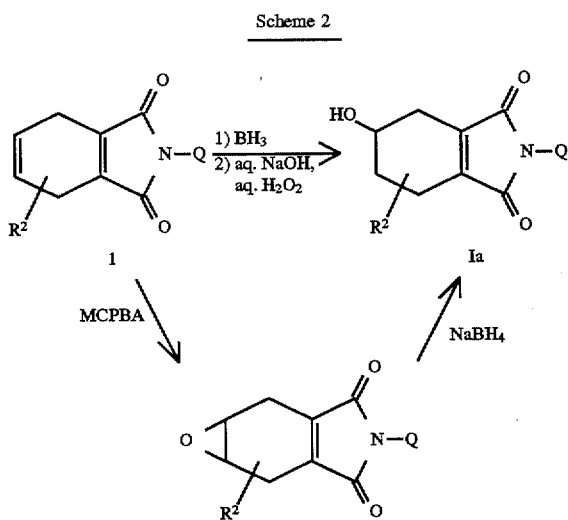

Alternatively, compounds of Formula Ia can be obtained by treatment of the olefin of Formula 1 with m-chloroperoxybenzoic acid (MCPBA) in an inert solvent such as dichloromethane to obtain the epoxide illustrated in Scheme 2. Subsequent treatment with a reducing agent such as sodium borohydride affords the alcohol of Formula Ia.

Compounds of Formula Ib (Scheme 3) are made from compounds of Formula Ia. The $R^{22}$ group is a subset of the $R^1$ group in compounds of Formula I. For example, treatment of the alcohol of Formula Ia with diethylaminosulfur trifluoride (DAST) at a temperature between about −78° C. and 100° C. in an inert solvent such as dichloromethane gives the fluorinated product of Formula Ib wherein $R^{22}$=F.

Scheme 3

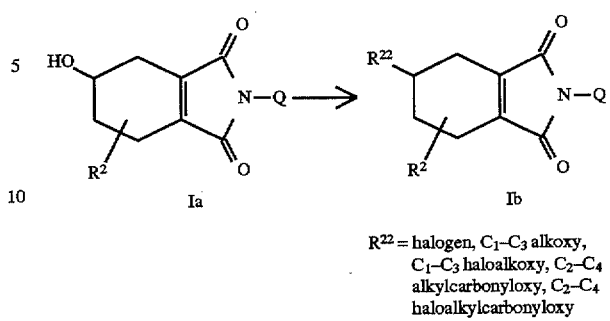

$R^{22}$ = halogen, $C_1$–$C_3$ alkoxy, $C_1$–$C_3$ haloalkoxy, $C_2$–$C_4$ alkylcarbonyloxy, $C_2$–$C_4$ haloalkylcarbonyloxy Compounds of Formula Ia can also be converted to the $R^{22}$=Cl, Br, and I compounds of Formula Ib using methods known to those skilled in the art (see March, J., *Advanced Organic Chemistry*, (1992), 4th Ed., John Wiley and Sons, Inc., pp 382–384). The hydroxy group in compounds of Formula Ia can be acylated by known methods to prepare the alkylcarbonyloxy and haloalkylcarbonyloxy derivatives (see March, J., *Advanced Organic Chemistry*, (1992), 4th Ed., John Wiley and Sons, Inc., pp 346–351). In-addition, the hydroxy or halo group can be convened by known methods to afford the alkoxy and haloalkoxy derivatives (see March, J., *Advanced Organic Chemistry*, (1992), 4th Ed., John Wiley and Sons, Inc., pp 342–346).

Compounds of Formula Ib wherein $R^{22}$=F can also be prepared directly from the unsaturated compound of Formula 1 by the addition of hydrofluoric acid. G. A. Olah and X. Y. Li, *Syn. Lett.*, (1990), 5, 267 and N. Yoneda et al., *Chem. Lett.*, (1984), 7, 1241 describe methods for the addition of HF to double bonds.

For some compounds of Formulae Ia and Ib wherein $R^2$ is other than hydrogen, the $R^2$ substituent is more conveniently introduced along with the $R^1$ substituent. This is especially the case when $R^1$ and $R^2$ are attached to the same carbon atom. For example, compounds of Formula Ib wherein $R^1$ and $R^2$ are gem-difluoro (compounds of Formula Id) can be prepared as illustrated in Scheme 4. Oxidation of the alcohol of Formula Ia wherein $R^2$ is hydrogen with pyridinium chlorochromate (PCC) in an inert solvent, such as dichloromethane, affords the ketone of Formula Ic. Subsequent treatment with DAST in dichloromethane as described above affords the gem-difluoro compound.

Scheme 4

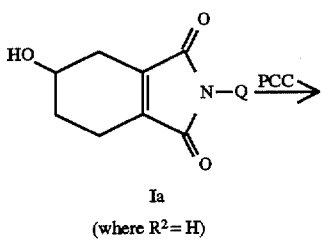

Ia
(where $R^2$ = H)

Scheme 4

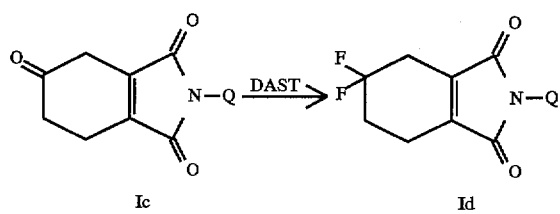

Similarly, as shown in Scheme 5, $R^1$ and $R^2$ can be introduced together when they are attached to adjacent carbons. Treatment of the olefin of Formula 1 (where $R^2$ is hydrogen) with NBS or NCS and water in an inert solvent such as DMSO at a temperature between about 0° C. and room temperature gives the bromohydrin of Formula Ie. Compounds of Formula If are made from compounds of Formula Ie. Treatment of the alcohol of Formula Ie with DAST at a temperature between about −78° C. and 100° C. in an inert solvent such as dichloromethane gives the fluorinated product of Formula If. Debromination or dechlorination can be achieved by treatment of Formula If with tributyltinhydride and AIBN at a temperature between about 0° C. and 150° C. in an inert solvent such as benzene or toluene to give the product of Formula Ig.

Scheme 5

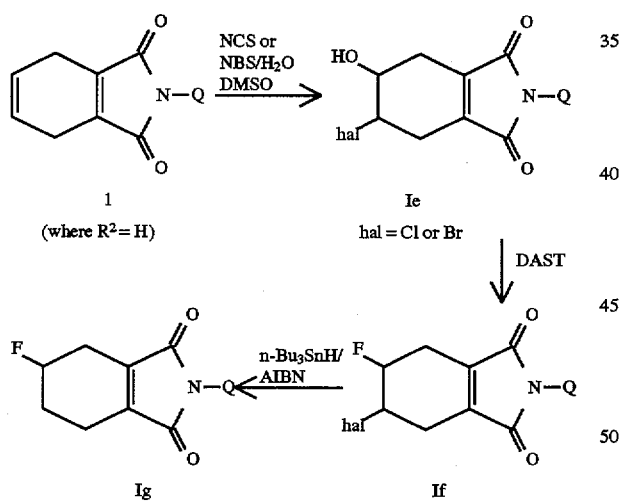

Yet another method for preparing compounds of Formula Ib is illustrated in Scheme 6. The appropriately substituted phthalic acid esters of Formula 2 can be reduced to form the cyclohexene diester of Formula 3 by hydrogenation over platinum (IV) oxide. Subsequent treatment with acid, such as hydrochloric acid affords the phthalic anhydride of Formula 4. Treatment with an aniline in acetic acid (AcOH) at a temperature between room temperature and reflux as described above, gives the dihydrophthalimide of Formula Ib.

Scheme 6

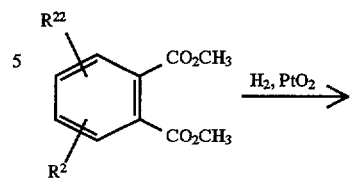

$R^{22}$ = halogen, $C_1$–$C_3$ alkoxy, $C_1$–$C_3$ haloalkoxy, $C_2$–$C_4$ alkylcarbonyloxy, $C_2$–$C_4$ haloalkylcarbonyloxy Compounds of Formula I wherein $R^2$ is hydrogen can be prepared by the methods illustrated in Schemes 7–10. Condensation of 3,4,5,6-tetrahydrophthalic anhydride ($q^1$=2) or its 5-membered ring homolog ($q^1$=1) with anilines in acetic acid (AcOH) at a temperature between ambient and reflux temperatures gives an imide of Formula 5, as illustrated in Scheme 7.

Scheme 7

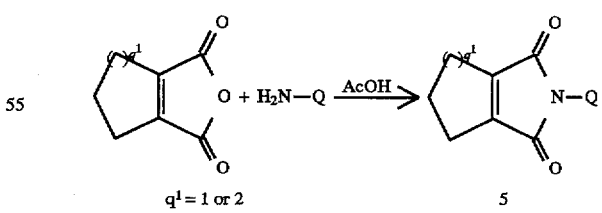

$q^1$ = 1 or 2

Treatment of the imide of Formula 5 with N-bromosuccinimide (NBS) in an inert solvent such as carbon tetrachloride at a temperature between ambient and reflux temperatures, in the presence of light, gives the allyl bromide of Formula Ih, as illustrated in Scheme 8.

Scheme 8

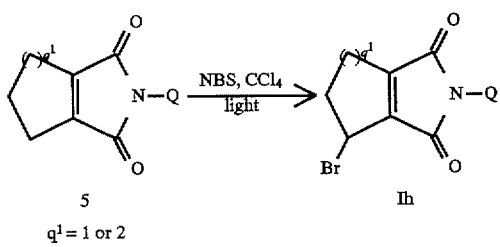

$q^1$ = 1 or 2

Hydrolysis of the bromide of Formula Ih using aqueous dimethyl sulfoxide (DMSO) at a temperature between about room temperature and the reflux temperature of the solvent gives the alcohol of Formula Ii (Scheme 9).

Scheme 9

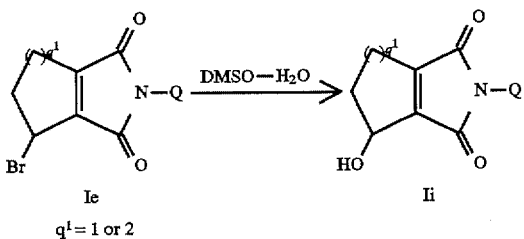

$q^1$ = 1 or 2

Compounds of Formula Ij (Scheme 10) can be made from alcohols of Formula Ii. For example, treatment of the alcohol of Formula Ii with diethylaminosulfur trifluoride (DAST) at a temperature between about −78° C. and 100° C. in an inert solvent such as dichloromethane gives the fluorinated product of Formula Ij wherein $R^{22}$=F. Compounds of Formula If can also be converted to compounds of Formula Ij wherein $R^{22}$=Cl, Br, I, alkylcarbonyloxy and haloalkylcarbonyloxy as described above for compounds of Formula Ib. Likewise, compounds of Formula Ij wherein $R^{22}$=alkoxy or haloalkoxy can be derived from the hydroxy (Id) or bromo (Ih) derivatives by known methods (see March, J., *Advanced Organic Chemistry*, (1992), 4th Ed., John Wiley and Sons, Inc., pp 382–384, 346–351,342–346).

Scheme 10

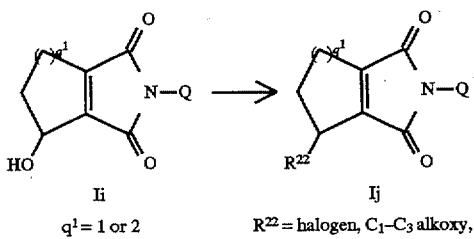

$q^1$ = 1 or 2
$R^{22}$ = halogen, $C_1$–$C_3$ alkoxy, $C_1$–$C_3$ haloalkoxy, $C_2$–$C_4$ alkylcarbonyloxy, $C_2$–$C_4$ haloalkylcarbonyloxy Compounds of Formula Ik can be prepared by the method illustrated in Scheme 11. Treatment of β-keto esters of Formula 6 with trifluoromethanesulfonic anhydride (triflic anhydride) affords the vinyl triflate of Formula 7 using conditions described in *Aldrichimica Acta*, (1983), 16, 15. Carbonylation of the vinyl triflate using carbon monoxide, palladium (II) acetate (Pd(OAc)$_2$) and 1,3-bis (diphenylphosphino)propane (dppp) provides the intermediate amide of Formula 8 (see R. E. Dolle et al., *J. Chem. Soc., Chem. Commun.*, (1987), 904; and S. Cacchi et at., *Tetrahedron Lett.*, (1985), 26, 1109 for a discussion of this carbonylation methodology). Cyclization occurs under basic conditions and/or upon heating to give the imide of Formula Ik.

Scheme 10

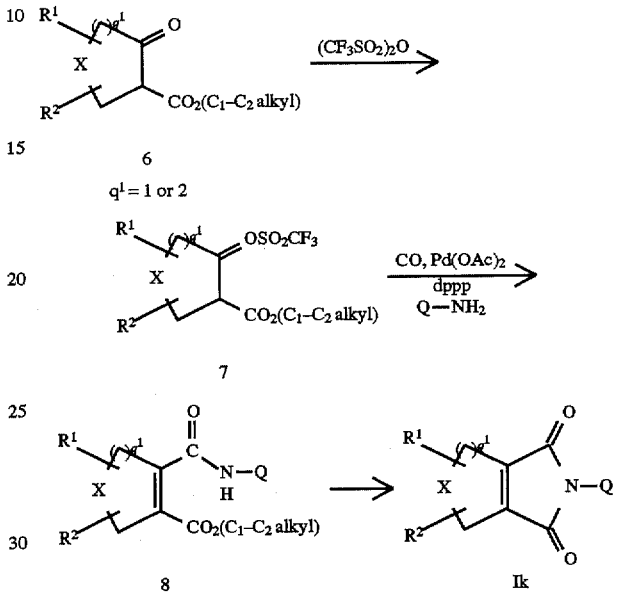

$q^1$ = 1 or 2

The β-ketoesters of Formula 6 are known or can be prepared by methods well-known in the art. For example, the ethyl ester of Formula 6 wherein X is S, $q^1$ is 2, and $R^1$ and $R^2$ are H is commercially available from Emka-Chemie, Schlusselberg, Germany. When X is a nitrogen-based group, it may be desirable to perform the reactions on a protected form of the nitrogen and introduce the desired X group after formation of the imide ring.

Compounds of Formula I wherein G is S can be prepared as illustrated in Scheme 12. Treatment of the amide-ester of Formula 8 with Lawesson's reagent (2,4-bis(4-methoxyphenyl)-1,3-dithia-2,4-diphosphetane-2,4-disulfide) affords the corresponding thioamide of Formula 9. Cyclization under the conditions described above (base and/or heat) affords the thioimide of Formula II. In instances where heat is necessary to convert the amide to the thioamide using Lawesson's reagent, the cyclized product may be obtained directly.

Scheme 12

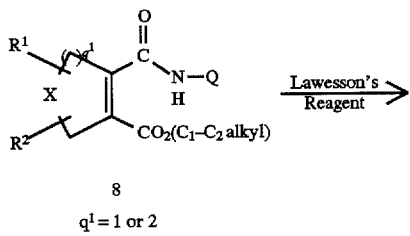

$q^1$ = 1 or 2

-continued
Scheme 12

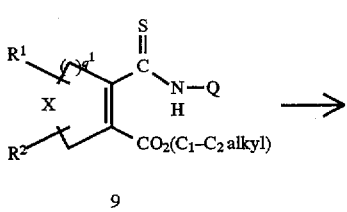

9

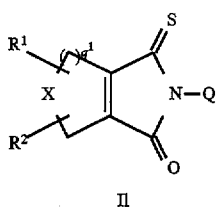

II

Compounds of Formula I wherein n+m=2 and the $R^{22}$-substituent on the cyclopentene ring is not in the allylic position (compounds of Formula In) can be prepared as illustrated in Scheme 13.

Scheme 13

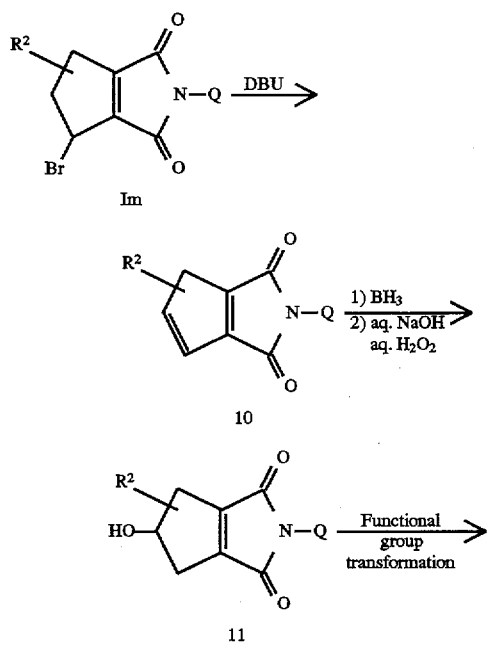

$R^{22}$ = halogen, $C_1$–$C_3$ alkoxy, $C_1$–$C_3$ haloalkoxy, $C_2$–$C_4$ alkylcarbonyloxy, $C_2$–$C_4$ haloalkylcarbonyloxy The bromo compound of Formula Im can be prepared by allylic bromination as described above and illustrated in Scheme 8. Treatment of the bromide with a strong base such as 1,8-diazabicyclo[5.4.0]undec-7-ene (DBU) leads to elimination of HBr and the formation of the unsaturated compound of Formula 10. Hydroboration using the conditions described above and illustrated in Scheme 2 affords the alcohol of Formula 11. If the ratio of alcohol regioisomers obtained in the hydroboration is undesirable, a larger mount of the desired regioisomer may be obtained by treatment of the olefin with mercuric acetate and water followed by demercuration with sodium borohydride. Conversion of the alcohol to the desired $R^{22}$ substituent can be accomplished in a manner analogous to those previously discussed (see above).

Compounds of Formula Io, compounds of Formula I wherein n or m is zero can be prepared as illustrated in Scheme 14. Treatment of the anhydride of Formula 12 with the appropriate aniline in acetic acid (HOAc) provides the imide of Formula Io. Arthydrides of Formula 12 are known or can be made by well-known methods. For example, the compound of Formula 12 wherein X is S, $R^1$ and $R^2$ are H, and $q^1$ is 2 is described in U.S. Pat. No. 4,164,404.

Scheme 14

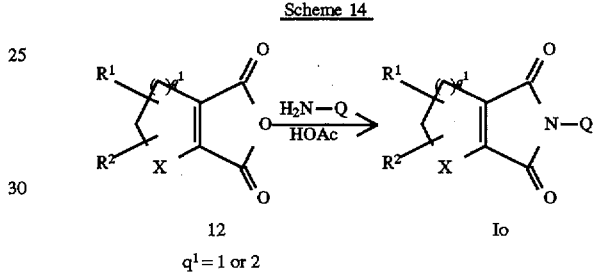

$q^1$ = 1 or 2

Synthesis for Compounds of Formula II

Treatment of the $R^2$-substituted tetrahydropyridazine (q=2) or pyrazoline (q=1) of Formula 13 with two equivalents of ethyl cyanoformate affords the 1,2-carboxylate of Formula 14 as illustrated in Scheme 15. The dicarboxylate can be converted to the triazolidinedione of Formula 15 by contact with trimethylaluminum in an inert solvent such as toluene or dichloromethane at a temperature between 0° C. and 100° C. followed by addition of the aniline $H_2NQ$ at a temperature between 0° C. and 100° C.

Scheme 15

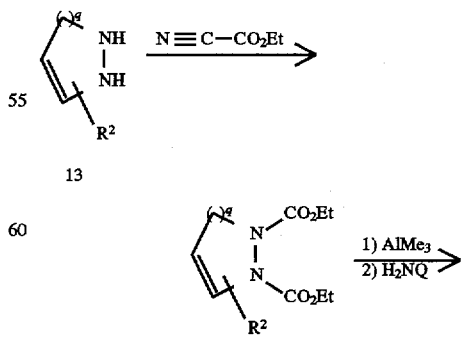

14

Scheme 15 (continued)

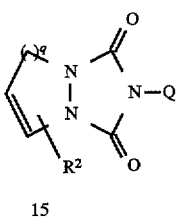

15

Treatment of the olefin of Formula 15 with borane in an inert solvent such as tetrahydrofuran at between about −78° C. and ambient temperature, followed by the addition of aqueous sodium hydroxide and hydrogen peroxide (preferably 30% aqueous) gives the alcohol of Formula IIa, as illustrated in Scheme 16. Alternatively, the alcohol of Formula IIa when q is 1 can be prepared from 4-hydroxypyrazolidine (see Kumagai, et al., *Heterocycles*, (1994), 37, 1521–7 for its preparation from epichlorohydrin and hydrazine) using the process described in Scheme 15.

Scheme 16

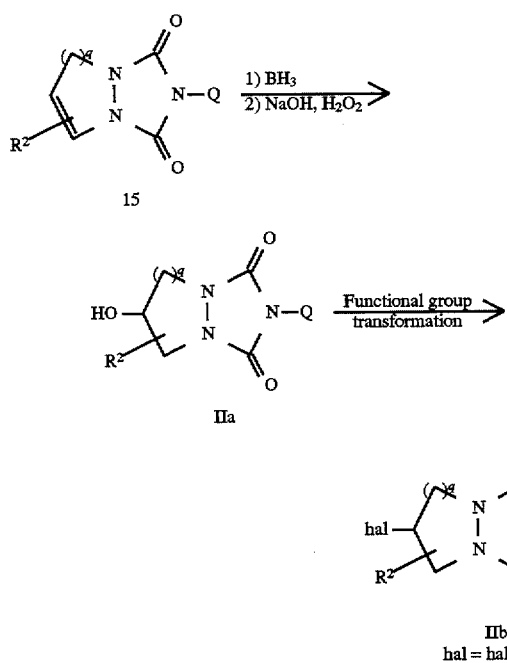

IIb
hal = halogen

Alcohols of Formula IIa a can be converted to the halo-substituted compounds of Formula IIb by well-known methods for performing this functional group transformation (see March, J., *Advanced Organic Chemistry*, (1992), 4th Ed., John Wiley and Sons, Incl, pp 382–384, 807–809). For example, treatment of the alcohol with diethylaminosulfur trifluoride (DAST) at a temperature between about −78° C. and 100° C. in an inert solvent such as dichloromethane gives the compound of Formula IIb wherein hal=F. Using the methods described in March above and known to those skilled in the art, compounds of Formula IIa can also be converted to compounds of Formula IIb wherein hal=Cl, Br, and I.

For some compounds of Formula IIb wherein $R^2$ is other than hydrogen, the $R^2$ substituent is more conveniently introduced along with the $R^1$ substituent. When $R^1$ and $R^2$ are both chlorine or bromine and attached to adjacent atoms, the halogens can be introduced in the same reaction by treating the olefin of Formula 15 with $Br_2$ or $Cl_2$ using standard conditions for dihalogenation. When $R^1$ and $R^2$ are gem-difluoro, the fluorine atoms can be introduced by treating the corresponding ketone with DAST as described above (see Scheme 4).

Compounds of Formula IIb wherein q is 2 (Formula IId can also be prepared using the reaction sequence described above starting with the tetrahydropyridazine of Formula 16 (Scheme 17).

Scheme 17

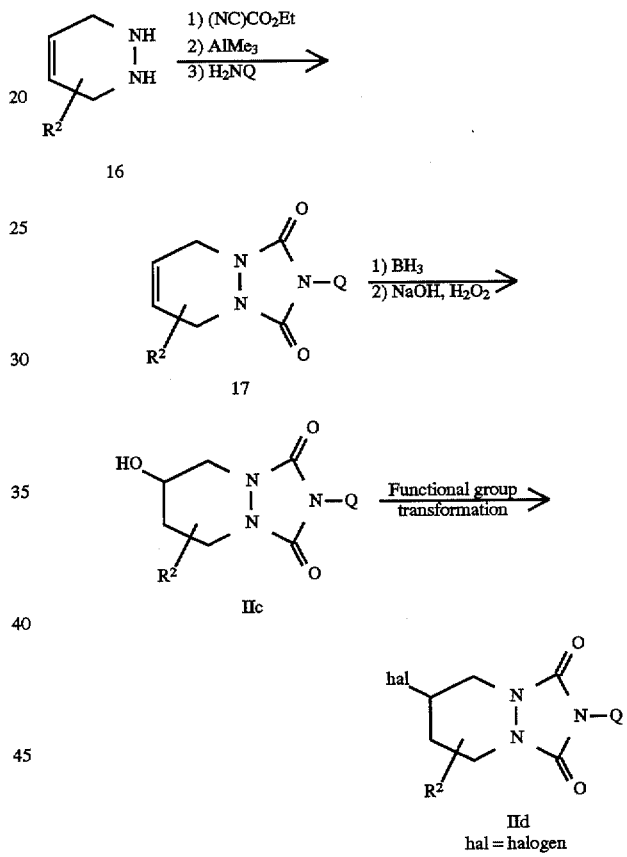

IId
hal = halogen

Compounds of Formulae IIe, IIf, and IIg can be prepared as shown in Scheme 18. Treatment of the olefin of Formula 17 (where $R^2$ is hydrogen) with NBS or NCS and water in an inert solvent such as DMSO at a temperature between about 0° C. and room temperature gives the bromohydrin of Formula IIe. Treatment of the alcohol of Formula IIe with DAST at a temperature between about −78° C. and 100° C. in an inert solvent such as dichloromethane gives the fluorinated product of Formula IIf. Debromination or dechlorination can be done by treatment of Formula IIf with tributyltin hydride and AIBN at a temperature between about 0° C. and 150° C. in an inert solvent such as benzene or toluene to give the product of Formula IIg.

Scheme 18

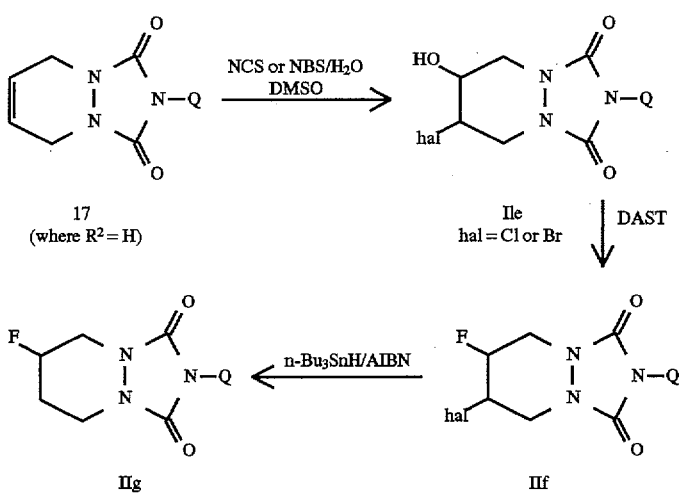

Compounds of Formula II wherein G is S can be prepared as illustrated in Scheme 19. Treatment of the $R^2$-substituted tetrahydropyridazine (q=2) or pyrazoline (q=1) of Formula 13 with the isothiocyanate derived from Q-NH$_2$ affords the thioamide of Formula 18. Cyclization can be accomplished by treatment of the aminoamide with 1,1'-carbonyldiimidazole and affords the thiono compound of Formula 19. In some instances, it is desirable to protect the non-acylated nitrogen of the tetrahydropyridazine or pyrazoline prior to contact with the isothiocyanate. The protecting group can be removed prior to cyclization. The thiono compound of Formula 19 can be converted to compounds of Formula II wherein G is S by the methods described above.

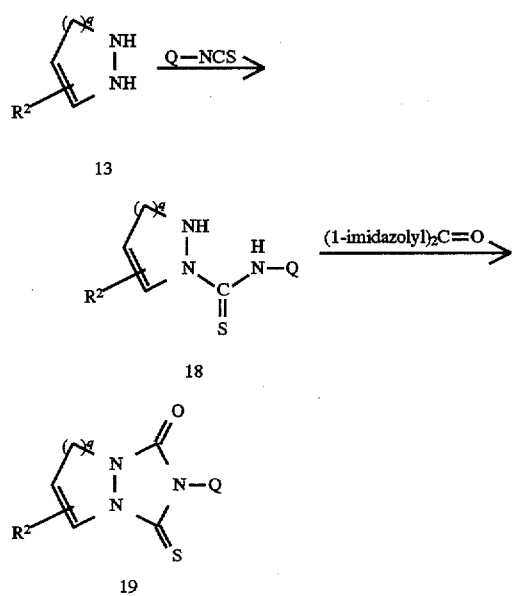

Compounds of Formula II can also be prepared by methods disclosed in EP-A-75,267 and illustrated in Scheme 20. Treatment of the urazol of Formula 20 with a base, such as sodium methoxide, sodium hydride, or n-butyllithium, in an inert solvent, such as methanol, diethyl ether, or tetrahydrofuran, at a temperature between about 60° C. and 160° C., followed by treatment with an alkylating agent of Formula 21 which is substituted at each terminus with a leaving group, affords the desired product. Appropriate leaving groups include chlorine, bromine, methane sulfonate, and p-toluene sulfonate. The $R^1$ and $R^2$ groups on the compound of Formula 21 may be substituted on any of the carbon atoms. Alternatively, protected forms of the $R^1$ and $R^2$ groups may be incorporated into 21, and then the actual $R^1$ and $R^2$ groups can be introduced after cyclization.

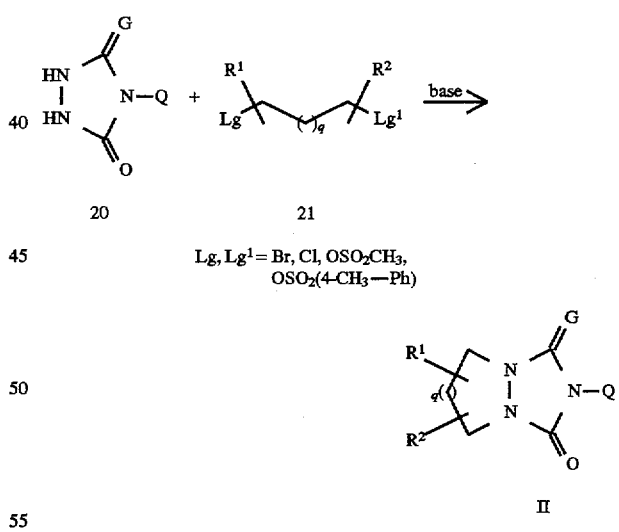

The anilines of formula Q-NH$_2$ and isothiocyanates of formula Q-NCS used as reactants in the syntheses described above are known or can be prepared by well-known methods. For example, anilines where Q is Q-1, Q-4, and Q-6 can be prepared as described in U.S. Pat. No. 4,902,335, anilines where Q is Q-2 and Q-3 can be prepared as described in U.S. Pat. No. 5,053,071, and anilines where Q is Q-5 can be prepared by well known functional group transformations of known phenyl derivatives.

It is recognized that some reagents and reaction conditions described above for preparing compounds of Formulae I and II may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991).

One skilled in the art will also recognize that compounds of Formulae I and II and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. $^1$H NMR spectra are reported in ppm downfield from tetramethylsilane; s=singlet, d=doublet, m=multiplet, br s=broad singlet, dm=doublet of multiplets.

EXAMPLE 1

Step A: Preparation of 2-(4-chloro-2-fluoro-5-hydroxyphenyl)4,7-dihydro-1-H-isindole-1.3(2H)-dione A mixture of 2.79 g (18.6 mmol) of 1,4-cyclohexadiene-1,2-dicarboxylic anhydride and 3.00 g (18.6 mmol) of 5-amino-2-chloro4-fluorophenol in 25 mL of acetic acid was warmed under reflux overnight. The mixture was then cooled to room temperature and concentrated under reduced pressure. The crude product was purified by flash chromatography over silica gel, eluting with a 1:3 v:v mixture of ethyl acetate and n-hexane to give 4.68 g of the title product of Step A as a yellow solid. $^1$H NMR (CDCl$_3$, 300 MHz) δ 3.1 (s, 4H), 5.6 (br s, 1H), 5.9 (s, 2H), 6.9 (d, 1H), 7.25 (d,1H).

Step B: Preparation of 2-(4-chloro-2-fluoro-5-hydroxyphenyl)-4,5,6,7-tetrahydro-5-hydroxy-1H-isoindole-1.3(2H)-dione To a solution of 500 mg(1.61 mmol) of 2-(4-chloro-2-fluoro-5-hydroxyphenyl)-4,7-dihydro-1H-isoindole-1,3 (2H)-dione in 10 mL of tetrahydrofuran (THF) was added 1.94 mL of a 1M solution of BH$_3$ in THF at 0° C. The mixture was then stirred at the same temperature for 1 h. Then, the mixture was warmed to room temperature. A solution of 3.0 mL of 6N aqueous sodium hydroxide, 1.8 mL of water, and 2.1 mL of 30% aqueous hydrogen peroxide were added subsequently. The mixture was stirred at the same temperature for 4 h. The crude product was diluted with ethyl acetate. The organic layer was washed with water, dried (MgSO$_4$) and concentrated under reduced pressure. The crude product was purified by flash chromatography over silica gel, eluting with a 1:2 v:v mixture of ethyl acetate and n-hexane to give 62 mg of the title product of Step B, a compound of the invention, as a yellow oil. $^1$H NMR (CDCl$_3$, 300 MHz) δ 1.8 (br s, 1H), 1.95 (m, 2H), 2.8–2.4 (m, 4H), 4.4 (m, 1H), 5.85 (br s, 1H), 6.9 (s, 1H), 7.5 (s, 1H).

EXAMPLE 2

Step A: Preparation of 2-(5-bezyloxy-4-chloro-2-fluorophenyl)-5,8-dihydro-1H-[1,2,4]triazolo[1,2-α] pyridazine-1,3(2H)-dione To a solution of 4.8 g of 4-chloro-2-fluoro-5-(phenylmethoxy)benzenamine (19.1 mmol) in 30 mL of toluene was added 11.5 mL of a 2.0M solution of trimethylaluminum (23.0 mmol) in toluene at room temperature. The mixture was stirred at the same temperature for 10 min. Then, 5.22 g of diethyl 1,2,3,6-tetrahydro-, 1,2-pyridazinedicarboxylate (22.9 mmol) was added at room temperature. The mixture was warmed under reflux overnight. The mixture was then cooled to room temperature and concentrated under reduced pressure. The crude product was purified by flash chromatography over silica gel, eluting with a 1:1 v:v mixture of ethyl acetate and n-hexane to give 6.20 g of the title product of Step A as a yellow solid melting at 165°–166° C. $^1$H NMR (CDCl$_3$, 300 MHz) δ 4.2 (s, 4H), 5.1 (s, 2H), 6.0 (s, 2H), 7.0 (d, 1H), 7.4 (m, 6H).

Step B: Preparation of 2-(5-benzloxy-4-chloro-2-fluorophenyl)-5,6,7,8,-tetrahydro-6-hydroxy-1H-[1,2,4]triazol[1,2-α]pyridazine-1,3(2H)-dione To a solution of 500 mg(1.33 mmol) of 2-(5-benzyloxy4-chloro-2-fluorophenyl)-5,8-dihydro-1H-[1,2,4]triazol[1,2-α]pyridazine-1,3(2H)-dione in 10 mL of THF was added 1.6 mL of a 1M solution of BH$_3$ in THF at 0° C. The mixture was then stirred at the same temperature for 1 h. Then, the mixture was warmed to room temperature. A solution of 2.5 mL of 6N aqueous sodium hydroxide, then 1.5 mL of water, and finally 1.7 mL of 30% aqueous hydrogen peroxide were added subsequently. The mixture was stirred at 0° C. for 4 h. The crude product was diluted with ethyl acetate. The organic layer was washed with water, dried (MgSO$_4$) and concentrated under reduced pressure. The crude product was purified by flash chromatography over silica gel, eluting with a 1:1 v:v mixture of ethyl acetate and n-hexane to give 415 mg of the title product of Step B as a white solid melting at 138°–140° C. $^1$H NMR (CDCl$_3$, 300 MHz) δ 2.0 (m, 2H), 2.2 (s, 1H), 3.8 (m, 4H), 4.2 (s, 1H), 5.1 (s, 2H), 7.0 (d, 1H) 7.4 (m,6H)

Step C: Preparation of 2-(5-benzyloxy-4-chloro-2-fluorophenyl)-6-chloro-5,6,7,8-tetrahydro-1H-[1,2,4] triazolo[1,2-α]pyridazine-1,3(2H)-dione A mixture of 212 mg (0.523 mmol) of 2-(5-benzyloxy-4-chloro-2-fluorophenyl)-5,6,7,8-tetrahydro-6-hydroxy-1H-[1,2,4]triazolo[1,2-α]pyridazine-1,3(2H)-dione (0.523 mmol), 76 μL of CCl$_4$ (0.784 mmol), and 206 mg of triphenylphosphine (0.784 mmol) in 8 mL of dichloromethane was warmed under reflux for 2h. The mixture was then concentrated under reduced pressure. The crude product was purified by flash chromatography over silica gel, eluting with a 1: 1 v:v mixture of ethyl acetate and n-hexane to give 200 mg of the title product of Step C, a compound of the invention, as a colorless oil. $^1$H NMR (CDCl$_3$, 300 MHz) δ 2.3 (m, 2H), 3.5 (m, 2H), 3.9 (m, 2H), 4.4 (m, 1H), 5.1 (s, 2H), 7.0 (d, 1H), 7.4 (m, 6H).

EXAMPLE 3

Preparation of 5-bromo-2-[4-chloro-2-fluoro-5-(2-propynyloxy)phenyl]-4,5,6,7-tetrahydro-6-hydroxy-1H-isoindole-1,3(2H)-dione and 5,6-dibromo-2-[4-chloro-2-fluoro-5-(2-propynyloxy)phenyl]-4.5 6,7-tetrahydro-1H-isoindole-1.3(2H)-dione To a solution of 960 mg (2.89 mmol) of 2-[4-chloro-2-fluoro-5-(2-propynyloxy)phenyl]-4,7-dihydro-1H-isoindole-1,3(2H)-dione in 15 mL of DMSO were added 771 mg (4.33 mmol) of NBS and 1.5 mL of water in sequence at room temperature. The mixture was then stirred at the same temperature for 30 min. The crude product was poured into 100 mL of water. The aqueous layer was extracted with three 100 mL portions of ethyl acetate. The organic layers were washed with water, dried (MgSO$_4$) and concentrated under reduced pressure. The crude product was purified by flash chromatography over silica gel eluting with a 5:95 v:v mixture of methanol and dichloromethane to give 535 mg of the first title product of Example 3, a compound of the invention, as a white solid melting at 65° C. $^1$H NMR (CDCl$_3$, 300 MHz) δ 2.5 (m, 1H), 2.6–3.4 (m, 5H), 4.35 (m, 2H), 4.8 (s, 2H), 7.0 (d, 1H) 7.3 (1H). In addition, 76 mg of the second title product of Example 3, a compound of the invention, was isolated as a white solid. $^1$H NMR (CDCl$_3$, 300 MHz) δ 2.6 (m, 1H), 3.2 (d, 2H), 3.6 (2d, 2H), 4.7 (d, 2H), 4.8 (s, 2H), 7.0 (d, 1H), 7.3 (d, 1H),

EXAMPLE 4

Preparation of 5-bromo-2-[4-chloro-2-fluoro-5-(2-propynyloxy)phenyl]6-fluoro-4,5,6,7-tetrahydro-1H-isoindole-1.3(2H)-dione To a solution of 995 mg (2.32 mmol) of 5-bromo-2-[4-chloro-2-fluoro-5-(2-propynyloxy)phenyl]-4,5,6,7-tetrahydro-6-hydroxy-1H-isoindole-1,3(2H)-dione in 15 mL of dichloromethane was added 430 µL of DAST at 0° C. The mixture was stirred at the same temperature for 1 h. The reaction mixture was then poured into 50 mL of cold water. The aqueous layer was extracted with three 50 mL portions of ethyl acetate. The organic layers were dried (MgSO$_4$) and concentrated under reduced pressure. The crude product was purified by flash chromatography over silica gel eluting with a 1:4 v:v mixture of ethyl acetate and n-hexane to give 626 mg of the title product of Example 4, a compound of the invention, as a whim solid melting at 135°–136.5° C.

EXAMPLE 5

Preparation of 2-[4-chloro-2-fluoro-5-(2-propynyloxy)phenyl]-5-fluoro-4,5,6,7-tetrahydro-1H-isoindole-1,3(2H)-dione A mixture of 526 mg (1.22 mmol) of 5-bromo-2-[4-chloro-2-fluoro-5-(2-propynyloxy)phenyl]-6-fluoro4,5,6,7-tetrahydro-1H-isoindole-1,3(2H)-dione, 822 mL of n-tributyltin hydride (3.06 mmol), and a catalytic amount of AIBN (2,2'-azobis[2-methylpropanenitrile]) in 20 mL of benzene was warmed under reflux for 1h. The mixture was then concentrated under reduced pressure. The crude product was purified by flash chromatography over silica gel eluting with a 1:4 v:v mixture of ethyl acetate and n-hexane to give 332 mg of the title product of Example 5, a compound of the invention, as a colorless oily film. $^1$H NMR (CDCl$_3$, 300 MHz) δ 1.8–2.0 (m, 2H), 2.3–2.9 (m, 5H), 4.8 (d, 2H), 5.22 (dm, J=50 Hz, 1H), 7.0 (d, 1H), 7.3 (d,1H).

By the procedures described herein the compounds of Formula Ip and IIh listed in Tables 1 to 13 can be prepared. The following abbreviations have been used in Tables 1–13:

TABLE 1

Compounds of Formula Ip wherein Q = Q-1; R$^5$ = Cl

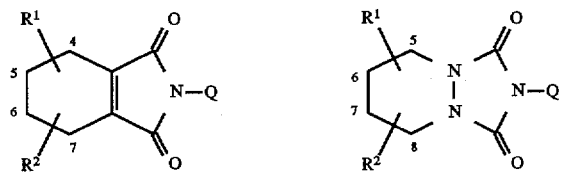

| Ip | | | | IIh | | | |
|---|---|---|---|---|---|---|---|
| R$^1$ | R$^2$ | R$^3$ | R$^4$ | R$^1$ | R$^1$ | R$^3$ | R$^4$ |
| 4-F | H | Cl | OCH$_2$C≡CH | 4-F | H | Cl | OCH(CH$_3$)C≡CH |
| 5-F | H | Cl | OCH$_2$C≡CH | 5-F | H | Cl | OCH(CH$_3$)C≡CH |
| 4-F | 4-F | Cl | OCH$_2$C≡CH | 4-F | 4-F | Cl | OCH(CH$_3$)C≡CH |
| 5-F | 5-F | Cl | OCH$_2$C≡CH | 5-F | 5-F | Cl | OCH(CH$_3$)C≡CH |
| 4-F | 5-F | Cl | OCH$_2$C≡CH | 4-F | 5-F | Cl | OCH(CH$_3$)C≡CH |
| 5-F | 6-F | Cl | OCH$_2$C≡CH | 5-F | 6-F | Cl | OCH(CH$_3$)C≡CH |
| 4-F | 7-F | Cl | OCH$_2$C≡CH | 4-F | 7-F | Cl | OCH(CH$_3$)C≡CH |
| 4-F | H | F | OCH$_2$C≡CH | 4-F | H | F | OCH(CH$_3$)C≡CH |
| 5-F | H | F | OCH$_2$C≡CH | 5-F | H | F | OCH(CH$_3$)C≡CH |
| 4-F | 4-F | F | OCH$_2$C≡CH | 4-F | 4-F | F | OCH(CH$_3$)C≡CH |
| 5-F | 5-F | F | OCH$_2$C≡CH | 5-F | 5-F | F | OCH(CH$_3$)C≡CH |
| 4-F | 5-F | F | OCH$_2$C≡CH | 4-F | 5-F | F | OCH(CH$_3$)C≡CH |
| 5-F | 6-F | F | OCH$_2$C≡CH | 5-F | 6-F | F | OCH(CH$_3$)C≡CH |
| 4-F | 7-F | F | OCH$_2$C≡CH | 4-F | 7-F | F | OCH(CH$_3$)C≡CH |
| 4-F | H | Cl | OCH(CH$_3$)$_2$ | 4-F | H | Cl | OCH$_2$CH=CH$_2$ |
| 5-F | H | Cl | OCH(CH$_3$)$_2$ | 5-F | H | Cl | OCH$_2$CH=CH$_2$ |

TABLE 1-continued

Compounds of Formula Ip wherein Q = Q-1; R⁵ = Cl

| R¹ | R² | R³ | R⁴ | R¹ | R¹ | R³ | R⁴ |
|---|---|---|---|---|---|---|---|
| 4-F | 4-F | Cl | OCH(CH$_3$)$_2$ | 4-F | 4-F | Cl | OCH$_2$CH=CH$_2$ |
| 5-F | 5-F | Cl | OCH(CH$_3$)$_2$ | 5-F | 5-F | Cl | OCH$_2$CH=CH$_2$ |
| 4-F | 5-F | Cl | OCH(CH$_3$)$_2$ | 4-F | 5-F | Cl | OCH$_2$CH=CH$_2$ |
| 5-F | 6-F | Cl | OCH(CH$_3$)$_2$ | 5-F | 6-F | Cl | OCH$_2$CH=CH$_2$ |
| 4-F | 7-F | Cl | OCH(CH$_3$)$_2$ | 4-F | 7-F | Cl | OCH$_2$CH=CH$_2$ |
| 4-Cl | H | Cl | OCH$_2$C≡CH | 4-Cl | H | Cl | OCH(CH$_3$)C≡CH |
| 5-Cl | H | Cl | OCH$_2$C≡CH | 5-Cl | H | Cl | OCH(CH$_3$)C≡CH |
| 4-Cl | 4-Cl | Cl | OCH$_2$C≡CH | 4-Cl | 4-Cl | Cl | OCH(CH$_3$)C≡CH |
| 5-Cl | 5-Cl | Cl | OCH$_2$C≡CH | 5-Cl | 5-Cl | Cl | OCH(CH$_3$)C≡CH |
| 4-Cl | 5-Cl | Cl | OCH$_2$C≡CH | 4-Cl | 5-Cl | Cl | OCH(CH$_3$)C≡CH |
| 5-Cl | 6-Cl | Cl | OCH$_2$C≡CH | 5-Cl | 6-Cl | Cl | OCH(CH$_3$)C≡CH |
| 4-Cl | 7-Cl | Cl | OCH$_2$C≡CH | 4-Cl | 7-Cl | Cl | OCH(CH$_3$)C≡CH |
| 4-Cl | H | F | OCH$_2$C≡CH | 4-Cl | H | F | OCH(CH$_3$)C≡CH |
| 5-Cl | H | F | OCH$_2$C≡CH | 5-Cl | H | F | OCH(CH$_3$)C≡CH |
| 4-Cl | 4-Cl | F | OCH$_2$C≡CH | 4-Cl | 4-Cl | F | OCH(CH$_3$)C≡CH |
| 5-Cl | 5-Cl | F | OCH$_2$C≡CH | 5-Cl | 5-Cl | F | OCH(CH$_3$)C≡CH |
| 4-Cl | 5-Cl | F | OCH$_2$C≡CH | 4-Cl | 5-Cl | F | OCH(CH$_3$)C≡CH |
| 5-Cl | 6-Cl | F | OCH$_2$C≡CH | 5-Cl | 6-Cl | F | OCH(CH$_3$)C≡CH |
| 4-Cl | 7-Cl | F | OCH$_2$C≡CH | 4-Cl | 7-Cl | F | OCH(CH$_3$)C≡CH |
| 4-F | H | Cl | OCF$_2$C≡CH | 4-F | H | F | OCF$_2$C≡CH |
| 5-F | H | Cl | OCF$_2$C≡CH | 5-F | H | F | OCF$_2$C≡CH |
| 4-F | 4-F | Cl | OCF$_2$C≡CH | 4-F | 4-F | F | OCF$_2$C≡CH |
| 5-F | 5-F | Cl | OCF$_2$C≡CH | 5-F | 5-F | F | OCF$_2$C≡CH |
| 4-F | 5-F | Cl | OCF$_2$C≡CH | 4-F | 5-F | F | OCF$_2$C≡CH |
| 5-F | 6-F | Cl | OCF$_2$C≡CH | 5-F | 6-F | F | OCF$_2$C≡CH |
| 4-F | 7-F | Cl | OCF$_2$C≡CH | 4-F | 7-F | F | OCF$_2$C≡CH |
| 5-CH$_3$S | H | Cl | OCH$_2$C≡CH | 5-CH$_3$S | 6-Br | Cl | OCH$_2$C≡CH |
| 5-CH$_3$S | H | Cl | OCH$_2$C≡CH | 5-CH$_3$S | 6-Br | Cl | OCH$_2$C≡CH |
| 5-CH$_3$S | H | Cl | OCH$_2$C≡CH | 5-CH$_3$S | 6-Br | F | OCH$_2$C≡CH |
| 5-CH$_3$S | H | Cl | OCH$_2$C≡CH | 5-CH$_3$S | 6-Br | F | OCH$_2$C≡CH |
| 5-CH$_3$S | H | F | OCH$_2$C≡CH | 5-CH$_3$S | 6-Cl | Cl | OCH$_2$C≡CH |
| 5-CH$_3$S | H | F | OCH$_2$C≡CH | 5-CH$_3$S | 6-Cl | Cl | OCH$_2$C≡CH |
| 5-CH$_3$S | H | F | OCH$_2$C≡CH | 5-CH$_3$S | 6-Cl | F | OCH$_2$C≡CH |
| 5-CH$_3$S | H | F | OCH$_2$C≡CH | 5-CH$_3$S | 6-Cl | F | OCH$_2$C≡CH |
| 5-CH$_3$S | H | Cl | OCH(CH$_3$)$_2$ | 5-CH$_3$S | 6-Br | Cl | OCH(CH$_3$)$_2$ |
| 5-CH$_3$S | H | Cl | OCH(CH$_3$)$_2$ | 5-CH$_3$S | 6-Br | Cl | OCH(CH$_3$)$_2$ |
| 5-CH$_3$S | H | Cl | OCH(CH$_3$)$_2$ | 5-CH$_3$S | 6-Br | F | OCH(CH$_3$)$_2$ |
| 5-CH$_3$S | H | Cl | OCH(CH$_3$)$_2$ | 5-CH$_3$S | 6-Br | F | OCH(CH$_3$)$_2$ |
| 5-CH$_3$S | H | F | OCH(CH$_3$)$_2$ | 5-CH$_3$S | 6-Cl | Cl | OCH(CH$_3$)$_2$ |
| 5-CH$_3$S | H | F | OCH(CH$_3$)$_2$ | 5-CH$_3$S | 6-Cl | Cl | OCH(CH$_3$)$_2$ |

TABLE 1-continued

Compounds of Formula Ip wherein Q = Q-1; R⁵ = Cl

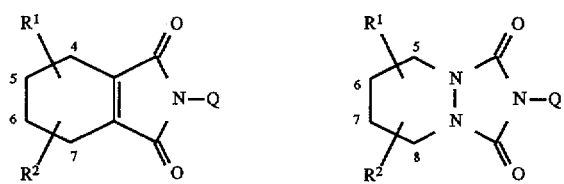

IpIIh

| R¹ | R² | R³ | R⁴ | R¹ | R¹ | R³ | R⁴ |
|---|---|---|---|---|---|---|---|
| 5-CH₃S | H | F | OCH(CH₃)₂ | 5-CH₃S | 6-Cl | F | OCH(CH₃)₂ |
| 5-CH₃S | H | F | OCH(CH₃)₂ | 5-CH₃S | 6-Cl | F | OCH(CH₃)₂ |
| 5-CH₃S | H | Cl | OCH₂CH=CH₂ | 5-CH₃S | 6-Br | Cl | OCH₂CH=CH₂ |
| 5-CH₃S | H | Cl | OCH₂CH=CH₂ | 5-CH₃S | 6-Br | Cl | OCH₂CH=CH₂ |
| 5-CH₃S | H | Cl | OCH₂CH=CH₂ | 5-CH₃S | 6-Br | F | OCH₂CH=CH₂ |
| 5-CH₃S | H | Cl | OCH₂CH=CH₂ | 5-CH₃S | 6-Br | F | OCH₂CH=CH₂ |
| 5-CH₃S | H | F | OCH₂CH=CH₂ | 5-CH₃S | 6-Cl | Cl | OCH₂CH=CH₂ |
| 5-CH₃S | H | F | OCH₂CH=CH₂ | 5-CH₃S | 6-Cl | Cl | OCH₂CH=CH₂ |
| 5-CH₃S | H | F | OCH₂CH=CH₂ | 5-CH₃S | 6-Cl | F | OCH₂CH=CH₂ |
| 5-CH₃S | H | F | OCH₂CH=CH₂ | 5-CH₃S | 6-Cl | F | OCH₂CH=CH₂ |
| 5-F | 6-Br | F | OCH₂C≡CH | 5-Br | 6-Br | F | OCH₂C≡CH |
| 5-F | 6-Br | F | OCH(CH₃)₂ | 5-Br | 6-Br | F | OCH(CH₃)₂ |
| 5-F | 6-Br | F | OCH₂CH=CH₂ | 5-Br | 6-Br | F | OCH₂CH=CH₂ |
| 5-F | 6-Br | Cl | OCH₂C≡CH | 5-Br | 6-Br | Cl | OCH₂C≡CH |
| 5-F | 6-Br | Cl | OCH(CH₃)₂ | 5-Br | 6-Br | Cl | OCH(CH₃)₂ |
| 5-F | 6-Br | Cl | OCH₂CH=CH₂ | 5-Br | 6-Br | Cl | OCH₂CH=CH₂ |
| 5-F | 6-Cl | F | OCH₂C≡CH | 5-Br | 6-Cl | F | OCH₂C≡CH |
| 5-F | 6-Cl | F | OCH(CH₃)₂ | 5-Br | 6-Cl | F | OCH(CH₃)₂ |
| 5-F | 6-Cl | F | OCH₂CH=CH₂ | 5-Br | 6-Cl | F | OCH₂CH=CH₂ |
| 5-F | 6-Cl | Cl | OCH₂C≡CH | 5-Br | 6-Cl | Cl | OCH₂C≡CH |
| 5-F | 6-Cl | Cl | OCH(CH₃)₂ | 5-Br | 6-Cl | Cl | OCH(CH₃)₂ |
| 5-F | 6-Cl | Cl | OCH₂CH=CH₂ | 5-Br | 6-Cl | Cl | OCH₂CH=CH₂ |
| 5,6-O— | | F | OCH₂C≡CH | 5,6-CH₂— | | F | OCH₂C≡CH |
| 5,6-O— | | F | OCH(CH₃)₂ | 5,6-CH₂— | | F | OCH(CH₃)₂ |
| 5,6-O— | | F | OCH₂CH=CH₂ | 5,6-CH₂— | | F | OCH₂CH=CH₂ |
| 5,6-O— | | Cl | OCH₂C≡CH | 5,6-CH₂— | | Cl | OCH₂C≡CH |
| 5,6-O— | | Cl | OCH(CH₃)₂ | 5,6-CH₂— | | Cl | OCH(CH₃)₂ |
| 5,6-O— | | Cl | OCH₂CH=CH₂ | 5,6-CH₂— | | Cl | OCH₂CH=CH₂ | n = normal
Ph = phenyl
Me = methyl
i = iso
Pr = propyl

TABLE 2

Compounds of Formula Ip wherein Q = Q – 1;

| R¹ | R² | R³ | R⁵ | R⁴ | R¹ | R² | R³ | R⁵ | R⁴ |
|---|---|---|---|---|---|---|---|---|---|
| 4-F | H | Cl | Br | OCH₂C≡CH | 4-Br | H | Cl | Cl | OCH₂C≡CH |
| 5-F | H | Cl | Br | OCH₂C≡CH | 5-Br | H | Cl | Cl | OCH₂C≡CH |
| 4-F | 4-F | Cl | Br | OCH₂C≡CH | 5-OMe | H | Cl | Cl | OCH₂C≡CH |
| 5-F | 5-F | Cl | Br | OCH₂C≡CH | 5-OCF₃ | H | Cl | Cl | OCH₂C≡CH |
| 4-F | 5-F | Cl | Br | OCH₂C≡CH | 4-MeC(O)O | H | Cl | Cl | OCH₂C≡CH |
| 5-F | 6-F | Cl | Br | OCH₂C≡CH | 6-CF₃C(O)O | H | Cl | Cl | OCH₂C≡CH |
| 4-F | 7-F | Cl | Br | OCH₂C≡CH | 5-F | 4-OH | Cl | Cl | OCH₂C≡CH |
| 5-carbonyl | | Cl | Cl | OCH₂C≡CH | 5-carbonyl | | Cl | Cl | OCH(CH₃)₂ |

TABLE 3

Compounds of Formula IIh wherein Q = Q – 1; R⁵ = Cl;

| $R^1$ | $R^2$ | $R^3$ | $R^4$ | $R^1$ | $R^2$ | $R^3$ | $R^4$ |
|---|---|---|---|---|---|---|---|
| H | 5-F | Cl | OCH₂C≡CH | H | 5-F | Cl | OCH(CH₃)C≡CH |
| H | 6-F | Cl | OCH₂C≡CH | H | 6-F | Cl | OCH(CH₃)C≡CH |
| 5-F | 5-F | Cl | OCH₂C≡CH | 5-F | 5-F | Cl | OCH(CH₃)C≡CH |
| 6-F | 6-F | Cl | OCH₂C≡CH | 6-F | 6-F | Cl | OCH(CH₃)C≡CH |
| 5-F | 6-F | Cl | OCH₂C≡CH | 5-F | 6-F | Cl | OCH(CH₃)C≡CH |
| 6-F | 7-F | Cl | OCH₂C≡CH | 6-F | 7-F | Cl | OCH(CH₃)C≡CH |
| 5-F | 8-F | Cl | OCH₂2≡CH | 5-F | 8-F | Cl | OCH(CH₃)C≡CH |
| H | 5-F | F | OCH₂C≡CH | H | 5-F | F | OCH(CH₃)C≡CH |
| H | 6-F | F | OCH₂C≡CH | H | 6-F | F | OCH(CH₃)C≡CH |
| 5-F | 5-F | F | OCH₂C≡CH | 5-F | 5-F | F | OCH(CH₃)C≡CH |
| 6-F | 6-F | F | OCH₂C≡CH | 6-F | 6-F | F | OCH(CH₃)C≡CH |
| 5-F | 6-F | F | OCH₂C≡CH | 5-F | 6-F | F | OCH(CH₃)C≡CH |
| 6-F | 7-F | F | OCH₂C≡CH | 6-F | 7-F | F | OCH(CH₃)C≡CH |
| 5-F | 8-F | F | OCH₂C≡CH | 5-F | 8-F | F | OCH(CH₃)C≡CH |
| H | 5-Cl | Cl | OCH₂C≡CH | H | 5-Cl | Cl | OCH(CH₃)C≡CH |
| H | 6-Cl | Cl | OCH₂C≡CH | H | 6-Cl | Cl | OCH(CH₃)C≡CH |
| 5-Cl | 5-Cl | Cl | OCH₂C≡CH | 5-Cl | 5-Cl | Cl | OCH(CH₃)C≡CH |
| 6-Cl | 6-Cl | Cl | OCH₂C≡CH | 6-Cl | 6-Cl | Cl | OCH(CH₃)C≡CH |
| 5-Cl | 6-Cl | Cl | OCH₂C≡CH | 5-Cl | 6-Cl | Cl | OCH(CH₃)C≡CH |
| 6-Cl | 7-Cl | Cl | OCH₂C≡CH | 6-Cl | 7-Cl | Cl | OCH(CH₃)C≡CH |
| 5-Cl | 8-Cl | Cl | OCH₂C≡CH | 5-Cl | 8-Cl | Cl | OCH(CH₃)C≡CH |
| H | 5-Cl | F | OCH₂C≡CH | H | 5-Cl | F | OCH(CH₃)C≡CH |
| H | 6-Cl | F | OCH₂C≡CH | H | 6-Cl | F | OCH(CH₃)C≡CH |
| 5-Cl | 5-Cl | F | OCH₂C≡CH | 5-Cl | 5-Cl | F | OCH(CH₃)C≡CH |
| 6-Cl | 6-Cl | F | OCH₂C≡CH | 6-Cl | 6-Cl | F | OCH(CH₃)C≡CH |
| 5-Cl | 6-Cl | F | OCH₂C≡CH | 5-Cl | 6-Cl | F | OCH(CH₃)C≡CH |
| 6-Cl | 7-Cl | F | OCH₂C≡CH | 6-Cl | 7-Cl | F | OCH(CH₃)C≡CH |
| 5-Cl | 8-Cl | F | OCH₂C≡CH | 5-Cl | 8-Cl | F | OCH(CH₃)C≡CH |
| H | 5-Cl | Cl | OCH(CH₃)₂ | H | 5-Cl | Cl | OCH₂CH=CH₂ |
| H | 6-Cl | Cl | OCH(CH₃)₂ | H | 6-Cl | Cl | OCH₂CH=CH₂ |
| 5-Cl | 5-Cl | Cl | OCH(CH₃)₂ | 5-Cl | 5-Cl | Cl | OCH₂CH=CH₂ |
| 6-Cl | 6-Cl | Cl | OCH(CH₃)₂ | 6-Cl | 6-Cl | Cl | OCH₂CH=CH₂ |
| 5-Cl | 6-Cl | Cl | OCH(CH₃)₂ | 5-Cl | 6-Cl | Cl | OCH₂CH=CH₂ |
| 6-Cl | 7-Cl | Cl | OCH(CH₃)₂ | 6-Cl | 7-Cl | Cl | OCH₂CH=CH₂ |
| 5-Cl | 8-Cl | Cl | OCH(CH₃)₂ | 5-Cl | 8-Cl | Cl | OCH₂CH=CH₂ |
| H | 5-F | Cl | OCF₂C≡CH | H | 5-F | F | OCF₂C≡CH |
| H | 6-F | Cl | OCF₂C≡CH | H | 6-F | F | OCF₂C≡CH |
| 5-F | 5-F | Cl | OCF₂C≡CH | 5-F | 5-F | F | OCF₂C≡CH |
| 6-F | 6-F | Cl | OCF₂C≡CH | 6-F | 6-F | F | OCF₂C≡CH |
| 5-F | 6-F | Cl | OCF₂C≡CH | 5-F | 6-F | F | OCF₂C≡CH |
| 6-F | 7-F | Cl | OCF₂C≡CH | 6-F | 7-F | F | OCF₂C≡CH |
| 5-F | 8-F | Cl | OCF₂C≡CH | 5-F | 8-F | F | OCF₂C≡CH |
| 5-CH₃S | H | Cl | OCH₂C≡CH | 5-CH₃S | 6-Br | Cl | OCH₂C≡CH |
| 5-CH₃S | H | Cl | OCH₂C≡CH | 5-CH₃S | 6-Br | Cl | OCH₂C≡CH |
| 5-CH₃S | H | Cl | OCH₂C≡CH | 5-CH₃S | 6-Br | F | OCH₂C≡CH |
| 5-CH₃S | H | Cl | OCH₂C≡CH | 5-CH₃S | 6-Br | F | OCH₂C≡CH |
| 5-CH₃S | H | F | OCH₂C≡CH | 5-CH₃S | 6-Cl | Cl | OCH₂C≡CH |
| 5-CH₃S | H | F | OCH₂C≡CH | 5-CH₃S | 6-Cl | Cl | OCH₂C≡CH |
| 5-CH₃S | H | F | OCH₂C≡CH | 5-CH₃S | 6-Cl | F | OCH₂C≡CH |
| 5-CH₃S | H | F | OCH₂C≡CH | 5-CH₃S | 6-Cl | F | OCH₂C≡CH |
| 5-CH₃S | H | Cl | OCH(CH₃)₂ | 5-CH₃S | 6-Br | Cl | OCH(CH₃)₂ |
| 5-CH₃S | H | Cl | OCH(CH₃)₂ | 5-CH₃S | 6-Br | Cl | OCH(CH₃)₂ |
| 5-CH₃S | H | Cl | OCH(CH₃)₂ | 5-CH₃S | 6-Br | F | OCH(CH₃)₂ |
| 5-CH₃S | H | Cl | OCH(CH₃)₂ | 5-CH₃S | 6-Br | F | OCH(CH₃)₂ |
| 5-CH₃S | H | F | OCH(CH₃)₂ | 5-CH₃S | 6-Cl | Cl | OCH(CH₃)₂ |
| 5-CH₃S | H | F | OCH(CH₃)₂ | 5-CH₃S | 6-Cl | Cl | OCH(CH₃)₂ |
| 5-CH₃S | H | F | OCH(CH₃)₂ | 5-CH₃S | 6-Cl | F | OCH(CH₃)₂ |
| 5-CH₃S | H | F | OCH(CH₃)₂ | 5-CH₃S | 6-Cl | F | OCH(CH₃)₂ |
| 5-CH₃S | H | Cl | OCH₂CH=CH₂ | 5-CH₃S | 6-Br | Cl | OCH₂CH=CH₂ |
| 5-CH₃S | H | Cl | OCH₂CH=CH₂ | 5-CH₃S | 6-Br | Cl | OCH₂CH=CH₂ |
| 5-CH₃S | H | Cl | OCH₂CH=CH₂ | 5-CH₃S | 6-Br | F | OCH₂CH=CH₂ |
| 5-CH₃S | H | Cl | OCH₂CH=CH₂ | 5-CH₃S | 6-Br | F | OCH₂CH=CH₂ |
| 5-CH₃S | H | F | OCH₂CH=CH₂ | 5-CH₃S | 6-Cl | Cl | OCH₂CH=CH₂ |
| 5-CH₃S | H | F | OCH₂CH=CH₂ | 5-CH₃S | 6-Cl | F | OCH₂CH=CH₂ |
| 5-CH₃S | H | F | OCH₂CH=CH₂ | 5-CH₃S | 6-Cl | F | OCH₂CH=CH₂ |
| 5-CH₃S | H | F | OCH₂CH=CH₂ | 5-CH₃S | 6-Cl | F | OCH₂CH=CH₂ |
| 5-F | 6-Br | F | OCH₂C≡CH | 5-Br | 6-Br | F | OCH₂=CH |
| 5-F | 6-Br | F | OCH(CH₃)₂ | 5-Br | 6-Br | F | OCH(CH₃)₂ |
| 5-F | 6-Br | F | OCH₂CH=CH₂ | 5-Br | 6-Br | F | OCH₂CH=CH₂ |
| 5-F | 6-Br | Cl | OCH₂C≡CH | 5-Br | 6-Br | Cl | OCH₂C≡CH |
| 5-F | 6-Br | Cl | OCH(CH₃)₂ | 5-Br | 6-Br | Cl | OCH(CH₃)₂ |
| 5-F | 6-Br | Cl | OCH₂CH=CH₂ | 5-Br | 6-Br | Cl | OCH₂CH=CH₂ |
| 5-F | 6-Cl | F | OCH₂C≡CH | 5-Br | 6-Cl | F | OCH₂C≡CH |
| 5-F | 6-Cl | F | OCH(CH₃)₂ | 5-Br | 6-Cl | F | OCH(CH₃)₂ |
| 5-F | 6-Cl | F | OCH₂CH=CH₂ | 5-Br | 6-Cl | F | OCH₂CH=CH₂ |

TABLE 3-continued

Compounds of Formula IIh wherein Q = Q – 1; $R^5$ = Cl;

| $R^1$ | $R^2$ | $R^3$ | $R^4$ | $R^1$ | $R^2$ | $R^3$ | $R^4$ |
|---|---|---|---|---|---|---|---|
| 5-F | 6-Cl | Cl | OCH$_2$C≡CH | 5-Br | 6-Cl | Cl | OCH$_2$C≡CH |
| 5-F | 6-Cl | Cl | OCH(CH$_3$)$_2$ | 5-Br | 6-Cl | Cl | OCH(CH$_3$)$_2$ |
| 5-F | 6-Cl | Cl | OCH$_2$CH=CH$_2$ | 5-Br | 6-Cl | Cl | OCH$_2$CH=CH$_2$ |
| 5,6-O— | | F | OCH$_2$C≡H | 5,6-CH$_2$— | | F | OCH$_2$C≡CH |
| 5,6-O— | | F | OCH(CH$_3$)$_2$ | 5,6-CH$_2$— | | F | OCH(CH$_3$)$_2$ |
| 5,6-O— | | F | OCH$_2$CH=CH$_2$ | 5,6-CH$_2$— | | F | OCH$_2$CH=CH$_2$ |
| 5,6-O— | | Cl | OCH$_2$CH≡CH | 5,6-CH$_2$— | | Cl | OCH$_2$C≡CH |
| 5,6-O— | | Cl | OCH(CH$_3$)$_2$ | 5,6-CH$_2$— | | Cl | OCH(CH$_3$)$_2$ |
| 5,6-O— | | Cl | OCH$_2$CH=CH$_2$ | 5,6-CH$_2$— | | Cl | OCH$_2$CH=CH$_2$ |

TABLE 4

Compounds of Formula IIh wherein Q = Q – 1;

| $R^1$ | $R^2$ | $R^3$ | $R^5$ | $R^4$ | $R^1$ | $R^2$ | $R^3$ | $R^5$ | $R^4$ |
|---|---|---|---|---|---|---|---|---|---|
| H | 5-F | Cl | Br | OCH$_2$C≡CH | 6-F | 7-F | Cl | Br | OCH$_2$C≡CH |
| H | 6-F | Cl | Br | OCH$_2$C≡CH | 5-F | 8-F | Cl | Br | OCH$_2$C≡CH |
| 6-F | 6-F | Cl | Br | OCH$_2$C≡CH | H | 5-Br | Cl | Cl | OCH$_2$C≡CH |
| 5-F | 5-F | Cl | Br | OCH$_2$C≡CH | H | 6-Br | Cl | Cl | OCH$_2$C≡CH |
| 5-F | 6-F | Cl | Br | OCH$_2$C≡CH | | | | | |

TABLE 5

Compounds of Formula Ip wherein Q = Q – 2; $R^5$ = Cl; $R^6$ = H; $R^7$ = Me; W = O;  Compounds of Formula IIb wherein Q = Q – 2; $R^5$ = Cl; $R^6$ = H; $R^7$ = Me; W = O;

| $R^1$ | $R^2$ | $R^3$ | $R^1$ | $R^2$ | $R^3$ | $R^1$ | $R^2$ | $R^3$ | $R^1$ | $R^2$ | $R^3$ |
|---|---|---|---|---|---|---|---|---|---|---|---|
| 4-F | H | Cl | 4-F | H | F | H | 5-F | Cl | H | 5-F | F |
| 5-F | H | Cl | 5-F | H | F | H | 6-F | Cl | H | 6-F | F |
| 5-F | 5-F | Cl | 5-F | 5-F | F | 5-F | 5-F | Cl | 5-F | 5-F | F |
| 4-F | 4-F | Cl | 4-F | 4-F | F | 6-F | 6-F | Cl | 6-F | 6-F | F |
| 4-F | 5-F | Cl | 4-F | 5-F | F | 5-F | 6-F | Cl | 5-F | 6-F | F |
| 5-F | 6-F | Cl | 5-F | 6-F | F | 6-F | 7-F | Cl | 6-F | 7-F | F |
| 4-F | 7-F | Cl | 4-F | 7-F | F | 5-F | 8-F | Cl | 5-F | 8-F | F |
| 4-Cl | H | Cl | 4-Cl | H | F | H | 5-Cl | Cl | H | 5-Cl | F |
| 5-Cl | H | Cl | 5-Cl | H | F | H | 6-Cl | Cl | H | 6-Cl | F |
| 4-Cl | 4-Cl | Cl | 4-Cl | 4-Cl | F | 5-Cl | 5-Cl | Cl | 5-Cl | 5-Cl | F |
| 5-Cl | 5-Cl | Cl | 5-Cl | 5-Cl | F | 6-Cl | 6-Cl | Cl | 6-Cl | 6-Cl | F |
| 4-Cl | 5-Cl | Cl | 4-Cl | 5-Cl | F | 5-Cl | 6-Cl | Cl | 5-Cl | 6-Cl | F |
| 5-Cl | 6-Cl | Cl | 5-Cl | 6-Cl | F | 6-Cl | 7-Cl | Cl | 6-Cl | 7-Cl | F |
| 4-Cl | 7-Cl | Cl | 4-Cl | 7-Cl | F | 5-Cl | 8-Cl | Cl | 5-Cl | 8-Cl | F |
| 5-F | 6-Br | F | 5-F | 6-Cl | F | 5-F | 6-Br | F | 5-F | 6-Cl | F |
| 5-F | 6-Br | Cl | 5-F | 6-Cl | Cl | 5-F | 6-Br | Cl | 5-F | 6-Cl | Cl |
| 5-Br | 6-Br | F | 5-Br | 6-Cl | F | 5-Br | 6-Br | F | 5-Br | 6-Cl | F |
| 5-Br | 6-Br | Cl | 5-Br | 6-Cl | Cl | 5-Br | 6-Br | Cl | 5-Br | 6-Cl | Cl |
| 5,6-O— | | F | 5,6-O— | | Cl | 5,6-O— | | F | 5,6-O— | | Cl |
| 5,6-CH$_2$— | | F | 5,6-CH$_2$— | | Cl | 5,6-CH$_2$— | | F | 5,6-CH$_2$— | | Cl |

TABLE 6

Compounds of Formula Ip wherein Q = Q – 6; W = O; $R^3$ = F; $R^6$ = H;

| $R^1$ | $R^2$ | $R^7$ | $R^8$ | $R^1$ | $R^2$ | $R^7$ | $R^8$ |
|---|---|---|---|---|---|---|---|
| 4-F | H | H | CH$_2$C≡CH | 4-F | H | H | CH(CH$_3$)C≡CH |
| 4-F | H | CH$_3$ | CH$_2$C≡CH | 4-F | H | CH$_3$ | CH(CH$_3$)C≡CH |
| 5-F | H | H | CH$_2$C≡CH | 5-F | H | H | CH(CH$_3$)C≡CH |
| 5-F | H | CH$_3$ | CH$_2$C≡CH | 5-F | H | CH$_3$ | CH(CH$_3$)C≡CH |
| 4-F | 4-F | H | CH$_2$C≡CH | 4-F | 4-F | H | CH(CH$_3$)C≡CH |

TABLE 6-continued

Compounds of Formula Ip wherein Q = Q – 6; W = O; $R^3$ = F; $R^6$ = H;

| $R^1$ | $R^2$ | $R^7$ | $R^8$ | $R^1$ | $R^2$ | $R^7$ | $R^8$ |
|---|---|---|---|---|---|---|---|
| 5-F | 5-F | H | $CH_2C\equiv CH$ | 5-F | 5-F | H | $CH(CH_3)C\equiv CH$ |
| 4-Cl | H | H | $CH_2C\equiv CH$ | 4-Cl | H | H | $CH(CH_3)C\equiv CH$ |
| 4-Cl | H | $CH_3$ | $CH_2C\equiv CH$ | 4-Cl | H | $CH_3$ | $CH(CH_3)C\equiv CH$ |
| 5-Cl | H | H | $CH_2C\equiv CH$ | 5-Cl | H | H | $CH(CH_3)C\equiv CH$ |
| 5-Cl | H | $CH_3$ | $CH_2C\equiv CH$ | 5-Cl | H | $CH_3$ | $CH(CH_3)C\equiv CH$ |
| 4-Cl | 4-Cl | H | $CH_2C\equiv CH$ | 4-Cl | 4-Cl | H | $CH(CH_3)C\equiv CH$ |
| 5-Cl | 5-Cl | H | $CH_2C\equiv CH$ | 5-Cl | 5-Cl | H | $CH(CH_3)C\equiv CH$ |
| 5-F | 6-Br | H | $CH_2C\equiv CH$ | 5-Br | 6-Br | H | $CH_2C\equiv CH$ |
| 5-F | 6-Br | $CH_3$ | $CH_2C\equiv CH$ | 5-Br | 6-Br | $CH_3$ | $CH_2C\equiv CH$ |
| 5-F | 6-Br | H | $C(CH_3)C\equiv CH$ | 5-Br | 6-Br | H | $C(CH_3)C\equiv CH$ |
| 5-F | 6-Br | $CH_3$ | $C(CH_3)C\equiv CH$ | 5-Br | 6-Br | $CH_3$ | $C(CH_3)C\equiv CH$ |
| 5-F | 6-Cl | H | $CH_2C\equiv CH$ | 5-Br | 6-Cl | H | $CH_2C\equiv CH$ |
| 5-F | 6-Cl | $CH_3$ | $CH_2C\equiv CH$ | 5-Br | 6-Cl | $CH_3$ | $CH_2C\equiv CH$ |
| 5-F | 6-Cl | H | $C(CH_3)C\equiv CH$ | 5-Br | 6-Cl | H | $C(CH_3)C\equiv CH$ |
| 5-F | 6-Cl | $CH_3$ | $C(CH_3)C\equiv CH$ | 5-Br | 6-Cl | $CH_3$ | $C(CH_3)C\equiv CH$ |
| 5,6-O— | | H | $CH_2C\equiv CH$ | 5,6-$CH_2$— | | H | $CH_2C\equiv CH$ |
| 5,6-O— | | $CH_3$ | $CH_2C\equiv CH$ | 5,6-$CH_2$— | | $CH_3$ | $CH_2C\equiv CH$ |
| 5,6-O— | | H | $C(CH_3)C\equiv CH$ | 5,6-$CH_2$— | | H | $C(CH_3)C\equiv CH$ |
| 5,6-O— | | $CH_3$ | $C(CH_3)C\equiv CH$ | 5,6-$CH_2$— | | $CH_3$ | $C(CH_3)C\equiv CH$ |

TABLE 7

Compounds of Formula IIh wherein Q = Q – 6; W = O; $R^3$ = F; $R^6$ = H;

| $R^1$ | $R^2$ | $R^7$ | $R^8$ | $R^1$ | $R^2$ | $R^7$ | $R^8$ |
|---|---|---|---|---|---|---|---|
| H | 5-F | H | $CH_2C\equiv CH$ | H | 5-F | H | $CH(CH_3)C\equiv CH$ |
| H | 5-F | $CH_3$ | $CH_2C\equiv CH$ | H | 5-F | $CH_3$ | $CH(CH_3)C\equiv CH$ |
| H | 6-F | H | $CH_2C\equiv CH$ | H | 6-F | H | $CH(CH_3)C\equiv CH$ |
| H | 6-F | $CH_3$ | $CH_2C\equiv CH$ | H | 6-F | $CH_3$ | $CH(CH_3)C\equiv CH$ |
| 5-F | 5-F | H | $CH_2C\equiv CH$ | 5-F | 5-F | H | $CH(CH_3)C\equiv CH$ |
| 6-F | 6-F | H | $CH_2C\equiv CH$ | 6-F | 6-F | H | $CH(CH_3)C\equiv CH$ |
| H | 5-Cl | H | $CH_2C\equiv CH$ | H | 5-Cl | H | $CH(CH_3)C\equiv CH$ |
| H | 5-Cl | $CH_3$ | $CH_2C\equiv CH$ | H | 5-Cl | $CH_3$ | $CH(CH_3)C\equiv CH$ |
| H | 6-Cl | H | $CH_2C\equiv CH$ | H | 6-Cl | H | $CH(CH_3)C\equiv CH$ |
| H | 6-Cl | $CH_3$ | $CH_2C\equiv CH$ | H | 6-Cl | $CH_3$ | $CH(CH_3)C\equiv CH$ |
| 5-Cl | 5-Cl | H | $CH_2C\equiv CH$ | 5-Cl | 5-Cl | H | $CH(CH_3)C\equiv CH$ |
| 6-Cl | 6-Cl | H | $CH_2C\equiv CH$ | 6-Cl | 6-Cl | H | $CH(CH_3)C\equiv CH$ |
| 5-F | 6-Br | H | $CH_2C\equiv CH$ | 5-Br | 6-Br | H | $CH_2C\equiv CH$ |
| 5-F | 6-Br | $CH_3$ | $CH_2C\equiv CH$ | 5-Br | 6-Br | $CH_3$ | $CH_2C\equiv CH$ |
| 5-F | 6-Br | H | $C(CH_3)C\equiv CH$ | 5-Br | 6-Br | H | $C(CH_3)C\equiv CH$ |
| 5-F | 6-Br | $CH_3$ | $C(CH_3)C\equiv CH$ | 5-Br | 6-Br | $CH_3$ | $C(CH_3)C\equiv CH$ |
| 5-F | 6-Cl | H | $CH_2C\equiv CH$ | 5-Br | 6-Cl | H | $CH_2C\equiv CH$ |
| 5-F | 6-Cl | $CH_3$ | $CH_2C\equiv CH$ | 5-Br | 6-Cl | $CH_3$ | $CH_2C\equiv CH$ |
| 5-F | 6-Cl | H | $C(CH_3)C\equiv CH$ | 5-Br | 6-Cl | H | $C(CH_3)C\equiv CH$ |
| 5-F | 6-Cl | $CH_3$ | $C(CH_3)C\equiv CH$ | 5-Br | 6-Cl | $CH_3$ | $C(CH_3)C\equiv CH$ |
| 5,6-O— | | H | $CH_2C\equiv CH$ | 5,6-$CH_2$— | | H | $CH_2C\equiv CH$ |
| 5,6-O— | | $CH_3$ | $CH_2C\equiv CH$ | 5,6-$CH_2$— | | $CH_3$ | $CH_2C\equiv CH$ |
| 5,6-O— | | H | $C(CH_3)C\equiv CH$ | 5,6-$CH_2$— | | H | $C(CH_3)C\equiv CH$ |
| 5,6-O— | | $CH_3$ | $C(CH_3)C\equiv CH$ | 5,6-$CH_2$— | | $CH_3$ | $C(CH_3)C\equiv CH$ |

TABLE 8

Compounds of Formula Ip wherein Q = Q – 1; $R^1$ = 5-F; $R^2$ = H; $R^5$ = Cl;

| $R^3$ | $R^4$ | $R^3$ | $R^4$ | $R^3$ | $R^4$ | $R^3$ | $R^4$ |
|---|---|---|---|---|---|---|---|
| Cl | H | Cl | $SCH_2C\equiv CH$ | Cl | $CH=CHCO_2$(i-Pr) | Cl | $OCH_2OCH_3$ |
| F | H | F | $SCH_2C\equiv CH$ | F | $CH=CHCO_2$(i-Pr) | F | $OCH_2OCH_3$ |
| Cl | O-(n-Pr) | Cl | $SCH(CH_3)C\equiv CH$ | Cl | $OCH_2CO_2$(i-Pr) | Cl | $SCH_2CO_2Et$ |
| F | O-(n-Pr) | F | $SCH(CH_3)C\equiv CH$ | F | $OCH_2CO_2$(i-Pr) | F | $SCH_2CO_2Et$ |
| Cl | $OCH_2CF_3$ | Cl | $NHSO_2CH_3$ | Cl | $OCH_2OPh$ | Cl | $OCH_2CO$(i-Pr) |

TABLE 8-continued

Compounds of Formula Ip wherein Q = Q − 1; $R^1$ = 5-F; $R^2$ = H; $R^5$ = Cl;

| $R^3$ | $R^4$ | $R^3$ | $R^4$ | $R^3$ | $R^4$ | $R^3$ | $R^4$ |
|---|---|---|---|---|---|---|---|
| Cl | CO$_2$(i-Pr) | F | NHSO$_2$CH$_3$ | F | OCH$_2$OPh | F | OCH$_2$CO(i-Pr) |
| F | CO$_2$(i-Pr) | Cl | OCH$_2$CO$_2$(n-pentyl) | F | OCH$_2$CO$_2$(n-pentyl) | | |

TABLE 9

Compounds of Formula IIh wherein Q = Q − 1; $R^1$ = H; $R^2$ = 6-F; $R^5$ = Cl;

| $R^3$ | $R^4$ | $R^3$ | $R^4$ | $R^3$ | $R^4$ | $R^3$ | $R^4$ |
|---|---|---|---|---|---|---|---|
| Cl | H | Cl | SCH$_2$C≡CH | Cl | CH=CHCO$_2$(i-Pr) | Cl | OCH$_2$OCH$_3$ |
| F | H | F | SCH$_2$C≡CH | F | CH=CHCO$_2$(i-Pr) | F | OCH$_2$OCH$_3$ |
| Cl | O-(n-Pr) | Cl | SCH(CH$_3$)C≡H | Cl | OCH$_2$CO$_2$(i-Pr) | Cl | SCH$_2$CO$_2$Et |
| F | O-(n-Pr) | F | SCH(CH$_3$)C≡CH | F | OCH$_2$CO$_2$(i-Pr) | F | SCH$_2$CO$_2$Et |
| Cl | OCH$_2$CF$_3$ | Cl | NHSO$_2$CH$_3$ | Cl | OCH$_2$OPh | Cl | OCH$_2$CO(i-Pr) |
| Cl | CO$_2$(i-Pr) | F | NHSO$_2$CH$_3$ | F | OCH$_2$OPh | F | OCH$_2$CO(i-Pr) |
| F | CO$_2$(i-Pr) | Cl | OCH$_2$CO$_2$(n-pentyl) | F | OCH$_2$CO$_2$(n-pentyl) | | |

TABLE 10

Compounds of Formula Ip wherein Q = Q − 4; W = S; $R^3$ = F

| $R^1$ | $R^2$ | $R^9$ | $R^1$ | $R^2$ | $R^9$ | $R^1$ | $R^2$ | $R^9$ |
|---|---|---|---|---|---|---|---|---|
| 4-F | H | CH$_2$C≡CH | 4-Cl | 4-Cl | CH$_2$C≡CH | 4-F | H | CH(CH$_3$)C≡CH |
| 4-F | H | CH$_2$C≡CH | 4-Cl | H | CH$_2$C≡CH | 5-F | H | CH(CH$_3$)C≡CH |
| 5-F | H | CH$_2$C≡CH | 4-Cl | H | CH$_2$C≡CH | 4-F | 4-F | CH(CH$_3$)C≡CH |
| 5-F | H | CH$_2$C≡CH | 5-Cl | H | CH$_2$C≡CH | 5-F | 5-F | CH(CH$_3$)C≡CH |
| 4-F | 4-F | CH$_2$C≡CH | 5-Cl | H | CH$_2$C≡CH | 4-Cl | H | CH(CH$_3$)C≡CH |
| 5-F | 5-F | CH$_2$C≡CH | 5-Cl | 5-Cl | CH$_2$C≡CH | 5-Cl | H | CH(CH$_3$)C≡CH |
| 6-F | 6-F | CH$_2$C≡CH | 5-Cl | 5-Cl | CH(CH$_3$)C≡CH | 4-Cl | 4-Cl | CH(CH$_3$)C≡CH |

TABLE 11

Compounds of Formula Ip wherein Q = Q − 3; Compounds of Formula IIh wherein Q = Q − 3;
$R^5$ = Cl; $R^6$ = H; $R^7$ = Me; W = O; $R^5$ = Cl; $R^6$ = H; $R^7$ = Me; W = O;

| $R^1$ | $R^2$ | $R^3$ | $R^1$ | $R^2$ | $R^3$ | $R^1$ | $R^2$ | $R^3$ | $R^1$ | $R^2$ | $R^3$ |
|---|---|---|---|---|---|---|---|---|---|---|---|
| 4-F | H | Cl | 4-F | H | F | 5-F | H | Cl | 5-F | H | F |
| 5-F | H | Cl | 5-F | H | F | 6-F | H | Cl | 6-F | H | F |
| 4-F | 4-F | Cl | 4-F | 4-F | F | 5-F | 5-F | Cl | 5-F | 5-F | F |
| 5-F | 5-F | Cl | 5-F | 5-F | F | 6-F | 6-F | Cl | 6-F | 6-F | F |
| 4-F | 5-F | Cl | 4-F | 5-F | F | 5-F | 6-F | Cl | 5-F | 6-F | F |
| 5-F | 6-F | Cl | 5-F | 6-F | F | 6-F | 7-F | Cl | 6-F | 7-F | F |
| 4-F | 7-F | Cl | 4-F | 7-F | F | 5-F | 8-F | Cl | 5-F | 8-F | F |
| 4-Cl | H | Cl | 4-Cl | H | F | 5-Cl | H | Cl | 5-Cl | H | F |
| 5-Cl | H | Cl | 5-Cl | H | F | 6-Cl | H | Cl | 6-Cl | H | F |
| 4-Cl | 4-Cl | Cl | 4-Cl | 4-Cl | F | 5-Cl | 5-Cl | Cl | 5-Cl | 5-Cl | F |
| 5-Cl | 5-Cl | Cl | 5-Cl | 5-Cl | F | 6-Cl | 6-Cl | Cl | 6-Cl | 6-Cl | F |
| 4-Cl | 5-Cl | Cl | 4-Cl | 5-Cl | F | 5-Cl | 6-Cl | Cl | 5-Cl | 6-Cl | F |
| 5-Cl | 6-Cl | Cl | 5-Cl | 6-Cl | F | 6-Cl | 7-Cl | Cl | 6-Cl | 7-Cl | F |
| 4-Cl | 7-Cl | Cl | 4-Cl | 7-Cl | F | 5-Cl | 8-Cl | Cl | 5-Cl | 8-Cl | F |

TABLE 12

Compounds of Formula Ip wherein Q = Q − 5; $R^6$ = $R^7$ = CF$_3$;

| $R^1$ | $R^2$ | $R^3$ | $R^1$ | $R^2$ | $R^3$ | $R^1$ | $R^2$ | $R^3$ | $R^1$ | $R^2$ | $R^3$ |
|---|---|---|---|---|---|---|---|---|---|---|---|
| 4-F | H | F | 4-F | 4-F | F | 4-Cl | 4-Cl | F | 4-F | 4-F | F |
| 4-F | H | Cl | 5-F | 5-F | Cl | 4-Cl | 4-Cl | Cl | 4-F | 4-F | Cl |
| 5-F | H | F | 4-Cl | H | F | 5-Cl | 5-Cl | F | 5-Cl | H | F |

TABLE 12-continued

| $R^1$ | $R^2$ | $R^3$ | $R^1$ | $R^2$ | $R^3$ | $R^1$ | $R^2$ | $R^3$ | $R^1$ | $R^2$ | $R^3$ |
|---|---|---|---|---|---|---|---|---|---|---|---|
| 5-F | H | Cl | 4-Cl | H | Cl | 5-Cl | 5-Cl | Cl | 5-Cl | H | Cl |

Compounds of Formula IIh wherein Q = Q − 5; $R^6$ = $R^7$ = CF$_3$;

| $R^1$ | $R^2$ | $R^3$ | $R^1$ | $R^2$ | $R^3$ | $R^1$ | $R^2$ | $R^3$ | $R^1$ | $R^2$ | $R^3$ |
|---|---|---|---|---|---|---|---|---|---|---|---|
| 5-F | H | F | 5-F | 5-F | F | 5-Cl | 5-Cl | F | 6-F | 6-F | F |
| 5-F | H | Cl | 5-F | 5-F | Cl | 5-Cl | 5-Cl | Cl | 6-F | 6-F | Cl |

TABLE 12-continued

| $R^1$ | $R^2$ | $R^3$ | $R^1$ | $R^2$ | $R^3$ | $R^1$ | $R^2$ | $R^3$ | $R^1$ | $R^2$ | $R^3$ |
|---|---|---|---|---|---|---|---|---|---|---|---|
| 6-F | H | F | 6-Cl | H | F | 6-Cl | 6-Cl | F | 6-Br | H | Cl |
| 6-F | H | Cl | 6-Cl | H | Cl | 6-Cl | 6-Cl | Cl | 5-OH | H | F |

TABLE 13

Compounds of Formula I and II wherein
Q = 4-Cl-2-F-5-(OCH$_2$C≡CH)—Ph;

| Formula I; $R^2$ = H | | | | | Formula II; | | | |
|---|---|---|---|---|---|---|---|---|
| $R^1$ | X | m | n | G | $R^1$ | $R^2$ | q | G |
| H | CHF | 1 | 1 | O | H | 5-F | 1 | O |
| H | CHF | 1 | 1 | S | H | 6-F | 1 | O |
| H | CHF | 1 | 2 | S | 5-F | 5-F | 1 | O |
| H | CF$_2$ | 1 | 1 | O | 6-F | 6-F | 1 | O |
| H | CF$_2$ | 1 | 1 | S | H | 5-F | 2 | S |
| H | CF$_2$ | 1 | 2 | S | H | 6-F | 2 | S |
| H | O | 0 | 3 | O | 5-F | 5-F | 2 | S |
| H | O | 1 | 2 | O | 6-F | 6-F | 2 | S |
| H | O | 1 | 1 | O | H | 5-F | 1 | S |
| H | S | 1 | 2 | O | H | 6-F | 1 | S |
| H | NMe | 1 | 2 | O | 5-F | 5-F | 1 | S |
| 4-F | CH$_2$ | 1 | 1 | O | 6-F | 6-F | 1 | S |
| 4-F | CHF | 1 | 1 | O | 5-F | 6-F | 1 | S |
| 4-Cl | CH$_2$ | 1 | 1 | O | 5-F | 6-F | 2 | S |
| 4-F | CH$_2$ | 1 | 1 | S | 5-F | 6-Cl | 2 | S |
| H | CHF | 1 | 1 | NH | H | 5-F | 1 | NH |
| H | CF$_2$ | 1 | 1 | NH | H | 6-F | 1 | NH |
| H | CHF | 1 | 2 | NH | 5-F | 5-F | 1 | NH |
| H | CF$_2$ | 1 | 2 | NH | 6-F | 6-F | 1 | NH |
| 4-F | CHF | 1 | 1 | NH | H | 5-F | 2 | NH |

Formulation/Utility

Compounds of this invention will generally be used in formulation with an agriculturally suitable carrier comprising a liquid or solid diluent and/or a surfactant wherein the formulation is consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective mounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5.50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., Handbook of Insecticide Dust Diluents and Carriers, 2nd Ed., Doffand Books, Caldwell, N.J. Typical liquid diluents are described in Marsden, Solvents Guide, 2nd Ed., Interscience, New York, 1950. McCutcheon's Detergents and Emulsifiers Annual, Allured Publ. Corp., Ridgewood, N.J., as well as Sisely and Wood, Encyclopedia of Surface Active Agents, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillinite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", Chemical Engineering, Dec. 4, 1967, pp 147–48, Perry's Chemical Engineer's Handbook, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the an of formulation, see U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A-C.

Example A

High Strength Concentrate

| | |
|---|---|
| Compound 18 | 98.5% |
| silica aerogel | 0.5% |
| synthetic amorphous fine silica | 1.0%. |

Example B

Wettable Powder

| | |
|---|---|
| Compound 18 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| Compound 18 | 10.0% |
| attapulgite granules (low volatile matter, 0.71/0.30 mm; U.S.S. No. 25-50 sieves) | 90.0%. |

Example D

Extruded Pellet

| | |
|---|---|
| Compound 18 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Tests results indicate that the compounds of the present invention are highly active preemergent and/or postemergent herbicides and/or plant growth regulants. Many of them have utility for broad-spectrum pre- and/or postemergence weed control in areas where complete control of all vegetation is desired such as around fuel storage tanks, industrial storage areas, parking lots, drive-in theaters, around billboards and highway and railroad structures. Some of the compounds are useful for the control of selected grass and broadleaf weeds with tolerance to important agronomic crops which include but are not limited to barley, cotton, wheat, rape, sugarbeets, corn, soybeans, rice, and plantation crops such as sugarcane, citrus, grapes, coffee, oil palm, cocoa, fruit trees, nut trees, banana, plantain, rubber, pineapple and loblolly pine. Preferred is the method of using compounds of Formulae I and II such as citrus, sugarcane, coffee, oil palm, rubber, cocoa, grapes, fruit trees, and pineapple.

Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. A mixture of one or more of the following herbicides with a compound of this invention may be particularly useful for weed control. Examples of other herbicides with which compounds of this invention can be formulated are: acetochlor, acifluorfen and its sodium salt, acrolein (2-propenal), alachlor, ametryn, amidosulfuron, amitrole, ammonium sulfamate, anilofos, asulam, atrazine, azimsulfuron, benazolin, benazolin-ethyl, benfluralin, benfuresate, bensulfuron-methyl, bensulide, bentazone, bifenox, bromacil, bromoxynil, bromoxynil octanoate, butachlor, butralin, butylate, chlomethoxyfen, chloramben, chlorbromuron, chloridazon, chlorimuron-ethyl, chlomitrofen, chlorotoluron, chlorpropham, chlorsulfuron, cklorthal-dimethyl, cinmethylin, cinosulfuron, clethodim, clomazone, clopyralid, clopyralid-olamine, cyaname, cycloate, cyclosulfamuron, 2,4-D and its butotyl, butyl, isoctyl and isopropyl esters and its dimethylammonium, diolamine and trolamine salts, daimuron, dalapon, dalaponsodium, dazomet, 2,4-DB and its dimethylammonium, potassium and sodium salts, desmedipham, desmetryn, dicamba and its dimethylammonium, potassium and sodium salts, dichlobenil, dichlorprop, diclofop-methyl, difenzoquat metilsulfate, diflourofenican, dimepiperate, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethyl α, 2-dichloro-5-[4-(difluoromethyl)-4, 5-dihydro-3-methyl-5-oxo-1H-1,2,4-triazol-1-yl]-4-flourobenzenepropanoate (F8426), fenoxaprop-ethyl, fenoxaprop-P-ethyl, fenuron, fenuron-TCA, flampropmethyl, flamprop-M-isopropyl, flamprop-M-methyl, flazasulfuron, fluazifop-butyl, fluazifop-P-butyl, fluchloralin, flumetsulam, fluroiclorac-pentyl, flouroioxazin, flouromemron, flouroglycofen-ethyl, flouropoxam, fluffdone, flurochloridone, flouroxypyr, fomesafen, losamine-ammonium, glucosinate, glufosinateammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, lactofen, lenaell, linuron, maleic hydrazide, MCPA and its dimethylammonium, potassium and sodium salts, MCPA-isoctyl, mecoprop, mecoprop-P, mefenacet, meflouroidide, metam-sodium, methabenzthiazuron, methyl [[2-chloro-4-fluoro-5-[ (tetrahydro-3-oxo-1H, 3H-[1,3,4]thiadiazolo[3,4-α] pyridazin-1-ylidene)amino]phenyl]thioacetate (KIH 9201), methylarsonic acid and its calcium, monoammonium, monosodium and disodium salts, methyl [[[1-[5-[2-chloro-4-(triflouromethyl)phenoxy]-2-nitrophenyl]-2-methoxyethylidene]amino]oxy]acetate (AKH-7088), methyl 5-[[[[(4,6-dimethyl-2-pyrimidinyl)amino]carbonyl] amino]sulfonyl]-1-(2-pyridinyl)-1H-pyrazole-4-carboxylate (NC-330), metobenzuron, metolachlor, metoxuron, metribuzin, metsulfuron-methyl, molinate, monolinuron, napropamide, naptalam, neburon, nicosulfuron, norflourorazon, oryzalin, oxadiazon, oxyfluororfen, paraquat dichloride, pebulate, pendimethalin, phenmedipham, picloram, picloram-potassium, pretilachlor, primisulfuron-methyl, prometon, prometryn, propachlor, propanil, propazine, propham, propyzamide, prosulfuron, pyrazolynate, pyrazosulfuron-ethyl, quinclorac, quizalofop-ethyl, quizalofop-P-ethyl, quizalofop-P-tefuryl, rirnsulfuron, sethoxydim, siduron, simazine, sulfentrazone, sulfometuron-methyl, TCA, TCA-sodium, tebuthiuron, terbacil, terbuthylazine, terbutryn, thenylchlor, thifensulfuron-methyl, thiobencarb, tralkoxydim, tri-allate, triasulfuron, tribenuron-methyl, triclopyr, triclopyr-butotyl, tridlopyr-triethylammonium, trifluralin, triflusulfuron-methyl, and vernolate.

In certain instances, combinations with other herbicides having a similar spectrum of control but a different mode of action will be particularly advantageous for management of resistant weeds.

A herbicidally effective mount of the compounds of this invention is determined by a number of factors. These factors include: formulation selected, method of application, amount and type of vegetation present, growing conditions, etc. In general, a herbicidally effective amount of a compound(s) of this invention is applied at rates from about 0.001 to 20 kg/ha with a preferred rate range of 0.004 to 1.0 kg/ha. One skilled in the art can easily determine application rates necessary for the desired level of weed control.

The following Tests demonstrate the control efficacy of the compounds of this invention against specific weeds. The weed control afforded by the compounds is not limited, however, to these species. See Index Tables A–C for compound descriptions.

Index TABLE A

| Cmpd No. | $R^1$ | $R^2$ | $R^3$ | $R^4$ | Stereo[a] | m.p. (°C.) |
|---|---|---|---|---|---|---|
| 1 | 4-Br | H | F | H | — | 79–82 |
| 2 | 4-Br | 7-Br | F | H | ND | 178–179.5 |
| 3 | 4-OH | H | F | H | — | solid[b] |
| 4 | 5-OH | H | Cl | OH | — | oil* |
| 5 | 4-Br | H | F | OC(=O)CH$_3$ | — | 61–64 |
| 6 | 4-Br | 7-Br | F | OC(=O)CH$_3$ | ND | 90–92 |
| 7 | 5-OH | H | F | OC(=O)CH$_3$ | — | solid* |
| 8 | 5,6-epoxy | | F | OCH$_2$C≡CH | cis | solid* |
| 9 | 6-SCH$_3$ | 5-F | F | OC(=O)CH$_3$ | trans | oil* |
| 10 | 5-OH | H | F | OCH$_2$C≡CH | — | oil* |
| 11 | 6-OH | 5-Cl | F | OCH$_2$Ph | trans | solid* |
| 12 | 6-OH | 5-F | F | OCH$_2$C≡CH | trans | solid* |
| 13 | 6-OH | 6-F | F | OCH$_2$C≡CH | cis | oil* |
| 14 | 6-OC(=O)CH$_3$ | 5-F | F | OCH$_2$C≡CH | trans | oil* |
| 15 | 6-Br | 5-Br | F | OCH$_2$Ph | trans | solid* |
| 16 | 6-Br | 5-F | F | OC(=O)CH$_3$ | cis | 144–144.5 |
| 17 | 6-OH | 5-Br | F | OC(=O)CH$_3$ | trans | 70–74 |
| 18 Ex. 5 | 5-F | H | F | OCH$_2$C≡CH | — | oil* |
| 19 | 6-Br | 5-Br | F | OC(=O)CH$_3$ | trans | solid* |
| 20 | 6-OH | 5-Br | F | OH | trans | gum* |
| 21 | 6-Br | 5-F | F | OH | cis | 78–80 |
| 22 Ex. 3 | 6-Br | 5-Br | F | OCH$_2$C≡CH | trans | solid* |
| 23 Ex. 3 | 6-OH | 5-Br | F | OCH$_2$C≡CH | trans | 65 (dec) |
| 24 Ex. 4 | 5-Br | 6-F | F | OCH$_2$C≡CH | cis | 135–136.5 |
| 25 | 6-OH | 5-Br | F | OCH$_2$Ph | trans | solid* |
| 26 | 4-OH | H | F | OH | — | oil* |
| 27 | 5,6-epoxy | | F | OH | cis | oil* |
| 28 | 5-OH | H | F | OCH$_3$ | — | oil* |
| 37 Ex. 1 | 5-OH | H | F | OH | — | oil* |

[a]This column indicates the stereochemistry of the compound. Trans and cis is the relative orientation between $R^1$ and $R^2$. ND indicates that the relative stereochemistry was not determined and the compound may be a mixture of diastereomers. A dash (—) indicates that only one diasteromer is possible since at least one of $R^1$ or $R^2$ is hydrogen. All compounds are racemic.
[b]Analysis: Calcd: C 56.87, H 3.75, N 4.74, Cl 11.99, F 6.42; Found: C 51.33, H 4.49, N 3.89, Cl 11.09, F 5.82.
*See Index Table C for $^1$H NMR data.

Index TABLE B

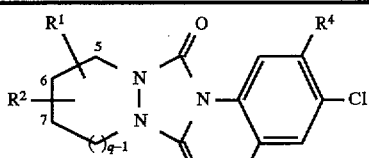

where q − 1 = 0 or 1

| Cmpd No. | R¹ | R² | q-1 | R³ | R⁴ | Stereo* | m.p. (°C.) |
|---|---|---|---|---|---|---|---|
| 29 | H | H | 0 | F | H | — | 110–128 |
| 30 | 6,7-epoxy | | 1 | Cl | OCH₂C≡CH | cis | oil* |
| 31 | 6,7-epoxy | | 1 | F | OCH₂Ph | cis | solid* |
| 32 | 7-SCH₃ | 6-F | 1 | F | OH | trans | oil* |
| 33ᵇ | 7-OH | 6-F | 1 | F | OH | trans | solid |
| 34 | 7-OH | 6-F | 1 | F | OCH₂C≡CH | trans | 155–157 |
| 35 | 7-OH | 6-Br | 1 | F | OCH₂Ph | trans | oil* |
| 36 Ex. 2 | H | 6-Cl | 1 | F | OCH₂Ph | — | oil* |

*This column indicates the stereochemistry of the compound. Trans and cis is the relative orientation between R¹ and R². A dash (—) indicates that only one diastereomer is possible since at least one of R¹ or R² is hydrogen. All compounds are racemic.
ᵇCompound contains approximately 47% by weight of the intermediate 2-[4-chloro-2-fluoro-5-hydroxyphenyl]-5,8-dihydro-1H-[1,2,4]triazolo[1,2-α]pyridazine-1,3(2H)-dione.
*See Index Table C for ¹H NMR data.

Index TABLE C

| Cmpd No. | ¹H NMR Data (CDCl₃ solution unless otherwise indicated)ᵃ |
|---|---|
| 4 | δ 1.80(s, 1H), 2.00(m, 2H), 2.46–2.80(m, 4H), 4.35(m, 1H), 5.9 (s, 1H), 6.90(s, 1H), 7.60(s, 1H). |
| 7 | δ 1.8(m, 2H), 2.4(s, 3H), 2.4–2.8(m, 4H), 4.3(m, 1H), 7.1(d, 1H) 7.4(d, 1H). |
| 8 | δ 2.6(m, 1H), 2.9(d, 2H), 3.2(d, 2H), 3.6(s, 2H), 4.75(d, 2H), 6.95(d, 1H), 7.3(d, 1H). |
| 9 | δ 2.25(s, 3H), 2.4(s, 3H), 2.7–3.05(m, 4H), 3.4(m, 1H), 5.12 (dm, 1H), 7.15(d, 1H), 7.4(d, 1H). |
| 10 | (in CD₃C(=O)CD₃) δ 2.9(m, 2H), 2.3–2.7(m, 4H), 2.9(m, 1H), 3.1(m, 1H), 4.3(m, 1H), 4.9(s, 2H), 7.3(d, 1H), 7.5(d, 1H). |
| 11 | δ 2.2(s, 1H), 2.5–3.2(m, 4H), 4.2(m, 2H), 5.1(s, 2H), 6.85(d, 1H), 7.3–7.5(m, 6H). |
| 12 | δ 2.2(br s, 1H), 2.6(m, 1H), 2.6–3.1(m, 4H), 4.4(m, 1H), 4.8 (d, 2H), 4.95(dq, J=55Hz, 1H), 7.0(d, 1H), 7.3(d, 1H). |
| 13 | δ 2.4–3.1(m, 5H), 3.9–4.4(m, 2H), 4.7(s, 2H), 5.0–5.2(m, 1H) 7.0(d, 1H), 7.3(d, 1H). |
| 14 | δ 2.1(s, 3H), 2.6(m, 1H), 2.7–2.95(m, 4H), 4.8(s, 2H), 5.1(dm, J=55Hz, 1H), 5.4(m, 1H), 7.0(d, 1H), 7.3(d, 1H). |
| 15 | δ 3.0–3.6(m, 4H), 4.6–4.8(m, 2H), 5.1(s, 2H), 6.9(d, 1H), 7.2–7.5(m, 6H). |
| 18 | δ 1.8–2.0(m, 2H), 2.3–2.9(m, 5H), 4.8(d, 2H), 5.22 (dm, J=50Hz, 1H), 7.0(d, 1H), 7.3(d, 1H). |
| 19 | δ 2.4(m, 3H), 3.2(m, 2H), 3.5–3.6(m, 2H), 4.7(m, 2H), 7.2(d, 1H), 7.4(d, 1H). |
| 20 | δ 2.6–2.7(m, 2H), 2.9–3.2(m, 2H), 3.4(m, 1H), 4.3(m, 2H), 5.9 (s, 1H), 6.9(d, 1H), 7.25(d, 1H). |
| 22 | δ 2.6(m, 1H), 3.2(d, 2H), 3.6(dd, 2H), 4.7(d, 2H), 4.8(s, 2H), 7.0(d, 1H), 7.3(d, 1H). |
| 25 | δ 2.6(m, 2H), 2.9–3.4(m, 3H), 4.3(m, 2H), 5.1(s, 2H), 6.9(d, 1H), 7.3–7.5(m, 6H). |
| 26 | δ 1.8–2.6(m, 6H), 2.7(br s, 1H), 4.8(m, 1H), 5.6(br s, 1H), 6.9 (d, 1H), 7.2(d, 1H). |
| 27 | δ 2.8(d, 2H), 3.1(d, 2H), 3.6(s, 2H), 6.9(d, 1H), 7.2(d, 1H), 8.1 (s, 1H). |
| 28 | (in CD₃C(=O)CD₃) δ 1.9(m, 2H), 2.1(m, 1H), 2.3–2.8(m, 4H), 3.9(s, 3H), 4.2(m, 1H), 7.2(d, 1H), 7.45(d, 1H). |
| 30 | δ 2.6(m, 1H), 3.6(s, 2H), 3.9–4.0(m, 2H), 4.1–4.3(m, 2H), 4.8 (s, 2H), 7.0(s, 1H), 7.6(s, 1H). |

Index TABLE C-continued

| Cmpd No. | ¹H NMR Data (CDCl₃ solution unless otherwise indicated)ᵃ |
|---|---|
| 31 | δ 3.6(s, 2H), 3.9(d, 2H), 4.1–4.25(d, 2H), 5.1(s, 2H), 6.9(d, 1H), 7.2–7.5(m, 6H). |
| 32 | δ 2.3(s, 3H), 3.9–4.2(m, 5H), 4.9(dm, J=55Hz, 1H), 5.9(s, 1H), 7.0(d, 1H), 7.3(d, 1H). |
| 35 | (in CD₃S(O)CD₃) δ 3.9(m, 3H), 4.05(m, 2H), 4.4(m, 1H), 5.2 (s, 2H), 6.2(d, 1H), 7.4–7.6(m, 6H), 7.8(d, 1H). |
| 36 | δ 2.3(m, 2H), 3.5(m, 2H), 3.9(m, 2H), 4.4(m, 1H), 5.1(s, 2H), 7.0(d, 1H), 7.4(m, 6H). |
| 37 | δ 1.8(br s, 1H), 1.95(m, 2H), 2.8–2.4(m, 4H), 4.4(m, 1H), 5.85 (br s, 1H), 6.9(s, 1H), 7.5(s, 1H). |

ᵃ¹H NMR data are in ppm downfield from tetramethylsilane. Couplings are designated by (s)-singlet, (d)-doublet, (q)-quartet, (m)-multiplet, (br s)-broad singlet, (dq)-doublet of quartets, (dm)-doublet of multiplets.

Test A

Seeds of barnyardgrass (*Echinochloa crus-galli*), cocklebur (*Xanthium pensylvanicum*), crabgrass (*Digitaria spp.*), downy brome (*Bromus tectorum*), giant foxtail (*Setaria faberii*), morningglory (*Ipomoea spp.*), sorghum (*Sorghum bicolor*), velvetleaf (*Abutilon theophrasti*) and wild oat (*Avena fatua*) were planted into a sandy loam soil and treated preemergence with test chemicals formulated in a nonphytotoxic solvent mixture which includes a surfactant. At the same time, these crop and weed species were also treated postemergence with test chemicals formulated in the same manner.

Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table A, are based on a 0 to 10 scale where 0 is no effect and 10 is complete control. A dash (-) response means no test results.

TABLE A

| | COMPOUND | | | COMPOUND | |
|---|---|---|---|---|---|
| Rate 2000 g/ha | 15 | 25 | Rate 1000 g/ha | 15 | 25 |
| POSTEMERGENCE | | | PREEMERGENCE | | |
| Barnyardgrass | 2 | 1 | Barnyardgrass | 4 | 4 |
| Cocklebur | 0 | 2 | Cocklebur | 5 | 3 |
| Crabgrass | 4 | 0 | Crabgrass | 2 | 2 |
| Downy brome | 0 | 0 | Downy brome | 3 | 3 |
| Giant foxtail | 7 | 8 | Giant foxtail | 3 | 3 |
| Morningglory | 0 | 1 | Morningglory | 9 | 7 |
| Sorghum | 1 | 1 | Sorghum | 5 | 3 |
| Velvetleaf | 2 | 4 | Velvetleaf | 10 | 10 |
| Wild oats | 0 | 1 | Wild oats | 4 | 3 |

Test B

Seeds of barley (*Hordeum vulgare*), barnyardgrass (*Echinochloa crus-galli*), blackgrass (*Alopecurus myosuroides*), bush bean (*Phaseolus vulgaris*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), giant foxtail (*Setariafaberii*), lambsquarters (*Chenopodium album*), morningglory (*Ipomoea hederacea*), rape (*Brassica napus*), rice (*Oryza satira*), sicklepod (*Cassia tora*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which includes a surfactant.

At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE B

| Rate 2000 g/ha | COMPOUND | | | | Rate 2000 g/ha | COMPOUND | | | |
|---|---|---|---|---|---|---|---|---|---|
| | 1 | 2 | 3 | 29 | | 1 | 2 | 3 | 29 |
| POSTEMERGENCE | | | | | PREEMERGENCE | | | | |
| Barley | — | — | — | — | Barnyardgrass | 9 | 8 | 8 | 10 |
| Barnyardgrass | 10 | 7 | 10 | 10 | Cocklebur | 8 | 0 | 1 | 10 |
| Bedstraw | — | — | — | — | Corn | 4 | 0 | 4 | 10 |
| Blackgrass | — | — | — | — | Crabgrass | 9 | 10 | 8 | 10 |
| Bush bean | 10 | 9 | 9 | 9 | Morningglory | 10 | 0 | 2 | 10 |
| Chickweed | — | — | — | — | Nutsedge | 9 | 0 | 0 | 9 |
| Cocklebur | 10 | 10 | 10 | 8 | Rice | 8 | 0 | 5 | 10 |
| Corn | 8 | 4 | 5 | 9 | Sicklepod | 10 | 0 | 4 | 10 |
| Cotton | 9 | 8 | 9 | 9 | Sorghum | 9 | 0 | 7 | 10 |
| Crabgrass | 10 | 8 | 8 | 10 | Soybean | 5 | 0 | 1 | 9 |
| Downy brome | — | — | — | — | Wheat | 9 | 0 | 8 | 10 |
| Giant foxtail | — | — | — | — | Wild oat | 8 | 0 | 3 | 9 |
| Lambsquarter | — | — | — | — | | | | | |
| Morningglory | 10 | 8 | 10 | 10 | | | | | |
| Nutsedge | 5 | 1 | 6 | 7 | | | | | |
| Rape | — | — | — | — | | | | | |
| Rice | 9 | 5 | 10 | 10 | | | | | |
| Sicklepod | 10 | 8 | 10 | 10 | | | | | |
| Sorghum | 10 | 4 | 10 | 10 | | | | | |
| Soybean | 9 | 7 | 8 | 9 | | | | | |
| Sugar beet | — | — | — | — | | | | | |
| Velvetleaf | — | — | — | — | | | | | |
| Wheat | 5 | 2 | 7 | 8 | | | | | |
| Wild buckwheat | — | — | — | — | | | | | |
| Wild oat | 9 | 2 | 7 | 8 | | | | | |

| | COMPOUND | | | | | | | | | | | | | | | | | | | | | | |
|---|---|---|---|---|---|---|---|---|---|---|---|---|---|---|---|---|---|---|---|---|---|---|---|
| | 4 | 5 | 6 | 8 | 9 | 10 | 11 | 12 | 13 | 14 | 16 | 17 | 18 | 19 | 20 | 21 | 22 | 23 | 24 | 30 | 31 | 32 | 33 | 34 |
| Rate 400 g/ha | | | | | | | | | | | | | | | | | | | | | | | | |
| POSTEMERGENCE | | | | | | | | | | | | | | | | | | | | | | | | |
| Barley | 0 | 0 | 0 | 5 | 4 | 6 | 1 | 5 | 3 | 6 | 5 | 1 | 10 | 5 | 2 | 5 | 8 | 8 | 9 | 0 | 3 | 1 | 2 | 9 |
| Barnyardgrass | 2 | 1 | 2 | 9 | 3 | 3 | 2 | 4 | 3 | 5 | 3 | 1 | 10 | 3 | 1 | 5 | 9 | 6 | 9 | 3 | 6 | 4 | 4 | 9 |
| Bedstraw | 0 | 4 | 4 | 9 | 3 | 9 | 6 | 10 | 7 | 10 | 7 | 3 | 10 | 7 | 2 | 6 | 10 | 10 | 10 | 4 | 6 | 6 | 3 | 10 |
| Blackgrass | 0 | 2 | 0 | 8 | 2 | 2 | 2 | 2 | 3 | 2 | 4 | 2 | 8 | 3 | 1 | 3 | 3 | 3 | 4 | 2 | 4 | 4 | 2 | 5 |
| Bush bean | — | — | — | — | — | — | — | — | — | — | — | — | — | — | — | — | — | — | — | — | — | — | — | — |
| Chickweed | 0 | 2 | 3 | 9 | 2 | 8 | 3 | 9 | 4 | 10 | 6 | 5 | 10 | 3 | 2 | 2 | 10 | 9 | 10 | 0 | 3 | 4 | 5 | 9 |
| Cocklebur | 4 | 3 | 6 | 10 | 6 | 8 | 4 | 9 | 7 | 8 | 7 | 4 | 10 | 7 | 6 | 5 | 10 | 9 | 9 | 4 | 8 | 3 | 6 | 9 |
| Corn | 0 | 2 | 2 | 4 | 3 | 3 | 1 | 3 | 3 | 3 | 3 | 2 | 5 | 2 | 1 | 1 | 3 | 3 | 3 | 3 | 3 | 2 | 2 | 9 |
| Cotton | 4 | 10 | 10 | 10 | 10 | 10 | 8 | 10 | 10 | 10 | 9 | 9 | 10 | 10 | 10 | 9 | 10 | 10 | 10 | 9 | 10 | 10 | 9 | 10 |
| Crabgrass | 0 | 3 | 2 | 5 | 4 | 3 | 2 | 5 | 4 | 4 | 5 | 2 | 9 | 4 | 3 | 3 | 8 | 6 | 8 | 3 | 6 | 2 | 3 | 8 |
| Downy brome | 0 | 0 | 0 | 5 | 1 | 2 | 2 | 1 | 2 | 3 | 5 | 1 | 8 | 2 | 1 | 3 | 4 | 3 | 5 | 0 | 5 | 3 | 1 | 3 |
| Giant foxtail | 0 | 2 | 3 | 7 | 4 | 3 | 2 | 4 | 3 | 5 | 4 | 1 | 10 | 3 | 2 | 2 | 9 | 6 | 7 | 3 | 6 | 3 | 2 | 4 |
| Lambsquarter | 1 | 6 | 4 | 10 | 5 | 10 | 9 | 10 | 9 | 10 | 8 | 7 | 10 | 7 | 3 | 8 | 10 | 10 | 10 | 10 | 9 | 6 | 7 | 10 |
| Morningglory | 0 | 0 | 1 | 10 | 6 | 10 | 4 | 10 | 6 | 10 | 8 | 3 | 10 | 10 | 4 | 4 | 10 | 10 | 10 | 8 | 8 | 8 | 5 | 10 |
| Nutsedge | 0 | — | — | 1 | 1 | 2 | 0 | 2 | 2 | 2 | — | — | — | — | — | — | — | — | — | 1 | 1 | 0 | — | — |
| Rape | 0 | 0 | 1 | 8 | 2 | 6 | 5 | 7 | 4 | 8 | 5 | 3 | 10 | 1 | 2 | 4 | 10 | 9 | 10 | 0 | 6 | 5 | 4 | 8 |
| Rice | 1 | 3 | 3 | 8 | 3 | 4 | 3 | 4 | 4 | 4 | 3 | 3 | 9 | 4 | 1 | 4 | 5 | 5 | 5 | 4 | 3 | 3 | 3 | 9 |
| Sicklepod | — | — | — | — | — | — | — | — | — | — | — | — | — | — | — | — | — | — | — | — | — | — | — | — |
| Sorghum | 1 | 3 | 2 | 4 | 3 | 3 | 2 | 4 | 3 | 3 | 4 | 3 | 9 | 5 | 3 | 5 | 5 | 4 | 5 | 4 | 4 | 3 | 3 | 7 |
| Soybean | 2 | 9 | 2 | 9 | 3 | 9 | 3 | 8 | 3 | 6 | 3 | 4 | 10 | 2 | 2 | 2 | 9 | 9 | 9 | 5 | 8 | 4 | 5 | 9 |
| Sugar beet | 3 | 2 | 8 | 10 | 9 | 9 | 7 | 10 | 6 | 10 | 9 | 8 | 10 | 10 | 9 | 10 | 10 | 10 | 10 | 6 | 8 | 7 | 8 | 10 |
| Velvetleaf | 0 | 3 | 5 | 10 | 3 | 10 | 7 | 10 | 9 | 10 | 6 | 6 | 10 | 10 | 3 | 6 | 10 | 10 | 10 | 7 | 9 | 2 | 7 | 10 |
| Wheat | 0 | 3 | 0 | 6 | 2 | 2 | 1 | 3 | 2 | 2 | 3 | 1 | 6 | 2 | 1 | 3 | 4 | 3 | 5 | 0 | 5 | 3 | 3 | 5 |
| Wild buckwheat | 1 | 6 | 3 | 10 | 6 | 10 | 7 | 10 | 10 | 10 | 8 | 6 | 10 | 3 | 1 | 7 | 10 | 10 | 10 | 5 | 9 | 7 | 6 | 10 |
| Wild oat | 0 | 2 | 2 | 6 | 1 | 2 | 2 | 1 | 1 | 1 | 4 | 1 | 10 | 3 | 1 | 3 | 4 | 3 | 4 | 0 | 3 | 3 | 2 | 5 |

TABLE B-continued

PREEMERGENCE

| | | | | | | | | | | | | | | | | | | | | | | | |
|---|---|---|---|---|---|---|---|---|---|---|---|---|---|---|---|---|---|---|---|---|---|---|---|
| Barley | 0 | 0 | 0 | 2 | 0 | 0 | 0 | 1 | 0 | 0 | 0 | 0 | 5 | 0 | 0 | 0 | 1 | 0 | 1 | 0 | 0 | 0 | 0 | 7 |
| Barnyardgrass | 0 | 0 | 0 | 3 | 0 | 4 | 0 | 7 | 3 | 6 | 3 | 0 | 9 | 0 | 0 | 0 | 3 | 3 | 5 | 0 | 2 | 0 | 3 | 9 |
| Bedstraw | 0 | 0 | 0 | 9 | 0 | 2 | 0 | 1 | 0 | 3 | 0 | 0 | 10 | 0 | 0 | 0 | 10 | 10 | 10 | 0 | 3 | 0 | 0 | 9 |
| Blackgrass | 0 | 0 | 0 | 3 | 0 | 0 | 0 | 0 | 0 | 0 | 0 | 0 | 9 | 0 | 0 | 0 | 6 | 2 | 3 | 1 | 0 | 0 | 0 | 6 |
| Chickweed | 0 | 0 | 0 | 7 | 0 | 2 | 0 | 6 | 0 | 6 | 0 | 0 | 10 | 0 | 0 | 0 | 10 | 8 | 10 | 0 | 0 | 0 | 0 | 10 |
| Cocklebur | 0 | 0 | 0 | 1 | 0 | 0 | 0 | 2 | 3 | 4 | 6 | 0 | 9 | 0 | 0 | 0 | 9 | 6 | 5 | 0 | 0 | 0 | 3 | 9 |
| Corn | 0 | 0 | 0 | 0 | 0 | 0 | 0 | 0 | 0 | 0 | 2 | 0 | 7 | 0 | 0 | 0 | 5 | 2 | 5 | 0 | 2 | 0 | 2 | 8 |
| Cotton | 0 | 0 | 0 | 0 | 0 | 8 | 0 | 6 | 3 | 0 | 3 | 0 | 8 | 0 | 0 | 0 | 6 | 0 | 0 | 0 | 7 | 0 | 3 | 7 |
| Crabgrass | 0 | 0 | 2 | 0 | 0 | 0 | 0 | 3 | 3 | 3 | 5 | 0 | 10 | 0 | 0 | 0 | 5 | 4 | 6 | 0 | 2 | 0 | 3 | 9 |
| Downy brome | 0 | 0 | 0 | 0 | 0 | 0 | 0 | 1 | 0 | 2 | 0 | 0 | 7 | 0 | 0 | 0 | 3 | 2 | 3 | 0 | 2 | 0 | 0 | 3 |
| Giant foxtail | 0 | 0 | 0 | 6 | 0 | 2 | 0 | 3 | 3 | 4 | 4 | 0 | 9 | 0 | 0 | 0 | 7 | 9 | 8 | 0 | 2 | 0 | 2 | 4 |
| Lambsquarter | 0 | 0 | 0 | 10 | 0 | 9 | 0 | 10 | 10 | 10 | 0 | 0 | 10 | 0 | 0 | 0 | 10 | 10 | 10 | 10 | 6 | 0 | 0 | 10 |
| Morningglory | 0 | 0 | 0 | 6 | 0 | 4 | 0 | 0 | 0 | 3 | 2 | 0 | 9 | 0 | 0 | 0 | 6 | 4 | 7 | 0 | 0 | 0 | 3 | 9 |
| Nutsedge | 0 | — | — | 0 | 0 | 0 | — | 0 | — | 0 | — | 0 | — | — | 0 | 0 | 3 | — | 3 | 0 | 0 | 0 | 5 | 3 |
| Rape | 0 | 0 | 0 | 8 | 0 | 0 | 0 | 0 | 0 | 0 | 0 | 0 | 10 | 0 | 0 | 0 | 10 | 3 | 4 | 0 | 0 | 0 | 0 | 9 |
| Rice | 0 | 0 | 0 | 0 | 0 | 4 | 0 | 2 | 0 | 2 | 3 | 0 | 6 | 0 | 0 | 0 | 0 | 0 | 2 | 0 | 0 | 0 | 3 | 9 |
| Sorghum | 0 | 0 | 0 | 0 | 0 | 3 | 0 | 2 | 2 | 0 | 2 | 0 | 7 | 0 | 0 | 0 | 2 | 2 | 2 | 0 | 0 | 0 | 0 | 5 |
| Soybean | 0 | 0 | 0 | 0 | 0 | 3 | 0 | 3 | 0 | 0 | 3 | 0 | 9 | 0 | 0 | 0 | 5 | 0 | 3 | 0 | 2 | 0 | 0 | 10 |
| Sugar beet | 0 | 0 | 0 | 9 | 0 | 0 | 0 | 6 | 0 | 5 | 0 | 0 | 10 | 0 | 0 | 0 | 9 | 8 | 9 | 3 | 3 | 3 | 6 | 7 |
| Velvetleaf | 0 | 0 | 9 | 9 | 0 | 4 | 0 | 7 | 0 | 5 | 3 | 0 | 10 | 0 | 0 | 0 | 10 | 10 | 10 | 0 | 7 | 0 | 3 | 10 |
| Wheat | 0 | 0 | 0 | 0 | 0 | 0 | 0 | 4 | 1 | 2 | 0 | 0 | 5 | 0 | 0 | 0 | 2 | 0 | 2 | 0 | 0 | 0 | 0 | 7 |
| Wild buckwheat | 0 | 0 | 0 | 9 | 0 | 0 | 0 | 5 | 0 | 6 | 0 | 0 | 10 | 0 | 0 | 0 | 10 | 9 | 9 | 0 | 0 | 0 | 0 | 10 |
| Wild oat | 0 | 0 | 0 | 0 | 0 | 0 | 0 | 1 | 0 | 1 | 0 | 0 | 10 | 0 | 0 | 0 | 10 | 8 | 8 | 0 | 2 | 0 | 0 | 6 |

Rate 100 g/ha

POSTEMERGENCE

| | | | | | | | | | | | | | | | | | | | | | | | |
|---|---|---|---|---|---|---|---|---|---|---|---|---|---|---|---|---|---|---|---|---|---|---|---|
| Barley | 0 | 0 | 0 | 7 | 3 | 4 | 1 | 5 | 2 | 5 | 3 | 0 | 7 | 4 | 1 | 3 | 7 | 7 | 7 | 0 | 3 | 0 | 2 | 7 |
| Barnyardgrass | 1 | 0 | 1 | 7 | 2 | 2 | 1 | 3 | 3 | 3 | 2 | 1 | 7 | 3 | 0 | 1 | 8 | 3 | 7 | 3 | 5 | 2 | 1 | 7 |
| Bedstraw | 0 | 2 | 2 | 10 | 2 | 7 | 3 | 8 | 5 | 9 | 7 | 3 | 10 | 5 | 1 | 2 | 10 | 8 | 10 | 2 | 6 | 6 | 2 | 8 |
| Blackgrass | 0 | 1 | 1 | 6 | 1 | 2 | 1 | 1 | 1 | 1 | 3 | 1 | 3 | 2 | 1 | 2 | 4 | 3 | 3 | 1 | 4 | 3 | 1 | 3 |
| Bush bean | — | — | — | — | — | — | — | — | — | — | — | — | — | — | — | — | — | — | — | — | — | — | — | — |
| Chickweed | 0 | 1 | 3 | 9 | 2 | 7 | 2 | 8 | 2 | 8 | 5 | 3 | 10 | 3 | 0 | 2 | 10 | 9 | 10 | 0 | 3 | 4 | 4 | 8 |
| Cocklebur | 2 | 3 | 5 | 9 | 5 | 4 | 2 | 7 | 3 | 7 | 6 | 2 | 10 | 6 | 2 | 2 | 9 | 8 | 9 | 4 | 5 | 2 | 4 | 8 |
| Corn | 0 | 1 | 1 | 3 | 2 | 3 | 1 | 3 | 3 | 3 | 2 | 1 | 2 | 2 | 0 | 1 | 2 | 3 | 2 | 3 | 2 | 1 | 2 | 4 |
| Cotton | 1 | 10 | 9 | 10 | — | 9 | 7 | 9 | 9 | 10 | 9 | 5 | 10 | 10 | 7 | 9 | 10 | 7 | 10 | 10 | 10 | 8 | 9 | 10 |
| Crabgrass | 0 | 2 | 2 | 6 | 2 | 3 | 1 | 5 | 4 | 4 | 5 | 0 | 6 | 4 | 0 | 2 | 7 | 6 | 7 | 3 | 3 | — | 1 | 5 |
| Downy brome | 0 | 0 | 0 | 5 | 1 | 1 | 0 | 1 | 1 | 1 | 4 | 1 | 4 | 2 | 0 | 2 | 3 | 3 | 3 | 0 | 3 | 0 | 0 | 3 |
| Giant foxtail | 0 | 2 | 2 | 6 | 2 | 3 | 2 | 3 | 3 | 4 | 4 | 1 | 6 | 3 | 0 | 2 | 7 | 4 | 7 | 3 | 5 | 3 | 1 | 2 |
| Lambsquarter | 1 | 2 | 1 | 10 | 3 | 8 | 7 | 9 | 6 | 10 | 7 | 5 | 10 | 6 | 1 | 7 | 10 | 10 | 10 | 7 | 9 | 3 | 6 | 10 |
| Morningglory | 0 | 0 | 2 | 10 | 4 | 10 | 2 | 10 | 6 | 9 | 6 | 2 | 10 | 7 | 4 | 2 | 10 | 9 | 10 | 7 | 6 | 2 | 3 | 10 |
| Nutsedge | 0 | 1 | — | — | 1 | 0 | — | 1 | 2 | 1 | — | — | 0 | — | — | — | — | — | — | 2 | — | 0 | — | — |
| Rape | 0 | 0 | 0 | 8 | 0 | 6 | 5 | 4 | 2 | 6 | 5 | 2 | 10 | — | 0 | 4 | 10 | 9 | 9 | 0 | 4 | 4 | 1 | 6 |
| Rice | 0 | 2 | 2 | 6 | 2 | 3 | 2 | 4 | 3 | 5 | 2 | 2 | 5 | 3 | 0 | 3 | 4 | 4 | 4 | 3 | 3 | 3 | 3 | 5 |
| Sicklepod | — | — | — | — | — | — | — | — | — | — | — | — | — | — | — | — | — | — | — | — | — | — | — | — |
| Sorghum | 0 | 2 | 2 | 4 | 3 | 3 | 2 | 5 | 2 | 3 | 3 | 2 | 6 | 4 | 2 | 3 | 4 | 3 | 4 | 3 | 3 | 3 | 3 | 6 |
| Soybean | 1 | 0 | 0 | 9 | 2 | 9 | 2 | 6 | 2 | 3 | 2 | 2 | 7 | 2 | 2 | 2 | 9 | 8 | 9 | 5 | 5 | 4 | 4 | 8 |
| Sugar beet | 0 | 0 | 0 | 9 | 8 | 6 | 4 | 10 | — | 9 | 7 | 6 | 10 | 9 | 2 | 7 | 10 | 10 | 10 | 5 | 6 | 7 | 5 | 9 |
| Velvetleaf | 0 | 0 | 1 | 10 | 2 | 9 | 6 | 7 | 8 | 10 | 3 | 1 | 10 | 6 | 3 | 2 | 10 | 9 | 10 | 5 | 9 | 1 | 2 | 10 |
| Wheat | 0 | 0 | 0 | 5 | 2 | 1 | 0 | 3 | 2 | 2 | 3 | 1 | 4 | 2 | 1 | 3 | 3 | 2 | 4 | 0 | 3 | 2 | 1 | 2 |
| Wild buckwheat | 1 | 2 | 1 | 10 | 1 | 10 | 6 | 10 | 9 | 10 | 7 | 1 | 10 | 3 | 1 | 3 | 10 | 10 | 10 | 1 | 9 | 4 | 3 | 10 |
| Wild oat | 0 | 0 | 0 | 6 | 1 | 2 | 1 | 2 | 1 | 2 | 3 | 1 | 4 | 2 | 0 | 3 | 3 | 2 | 3 | 0 | 3 | 2 | 1 | 3 |

PREEMERGENCE

| | | | | | | | | | | | | | | | | | | | | | | | |
|---|---|---|---|---|---|---|---|---|---|---|---|---|---|---|---|---|---|---|---|---|---|---|---|
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 5 |
| Barnyardgrass | 0 | 0 | 0 | 0 | 0 | 0 | 0 | 0 | 0 | 4 | 3 | 0 | 3 | 0 | 0 | 0 | 2 | 0 | 3 | 0 | 0 | 0 | 3 | 5 |
| Bedstraw | 0 | 0 | 0 | — | 0 | 0 | 0 | 0 | 0 | — | 0 | 10 | 0 | 0 | 0 | 10 | 1 | 10 | 0 | 0 | 0 | 0 | 0 | 8 |
| Blackgrass | 0 | 0 | 0 | 0 | 0 | 0 | 0 | 0 | 0 | 0 | 0 | 0 | 2 | 0 | 0 | 0 | 1 | 2 | 1 | 0 | 0 | 0 | 0 | 2 |
| Chickweed | 0 | 0 | 0 | 0 | 0 | 0 | 0 | 0 | 0 | 0 | 0 | 0 | 8 | 0 | 0 | 0 | 8 | 0 | 9 | 0 | 0 | 0 | 0 | 7 |
| Cocklebur | 0 | 0 | 0 | 0 | 0 | 0 | 0 | 0 | — | 3 | 3 | 0 | 2 | 0 | 0 | 0 | 0 | 0 | 0 | 0 | 0 | 0 | 3 | 7 |
| Corn | 0 | 0 | 0 | 0 | 0 | 0 | 0 | 0 | 0 | 0 | 2 | 0 | 3 | 0 | 0 | 0 | 2 | 0 | 0 | 0 | 0 | 0 | 2 | 7 |
| Cotton | 0 | 0 | 0 | 0 | 0 | 0 | 0 | 0 | 0 | 0 | 4 | 0 | 2 | 0 | 0 | 0 | 3 | 0 | 0 | 0 | 0 | 0 | 0 | 2 |
| Crabgrass | 0 | 0 | 0 | 0 | 0 | 0 | 0 | 0 | 0 | 0 | 3 | 0 | 6 | 0 | 0 | 0 | 3 | 0 | 3 | 0 | 0 | 0 | 4 | 3 |
| Downy brome | 0 | 0 | 0 | 0 | 0 | 0 | 0 | 2 | 0 | 2 | 0 | 0 | 3 | 0 | 0 | 0 | 3 | 3 | 2 | 0 | 0 | 0 | 0 | 2 |
| Giant foxtail | 0 | 0 | 0 | 0 | 0 | 0 | 0 | 0 | 0 | 0 | 3 | 0 | 2 | 0 | 0 | 0 | 0 | 0 | 0 | 0 | 0 | 0 | 2 | 0 |
| Lambsquarter | 0 | 0 | 0 | 10 | 0 | 6 | 0 | 9 | 2 | 9 | 0 | 0 | 10 | 0 | 0 | 0 | 10 | 10 | 9 | 8 | 0 | 0 | 0 | 10 |
| Morningglory | 0 | 0 | 0 | 0 | 0 | 0 | 0 | 0 | 1 | 2 | 0 | 6 | 0 | 0 | 0 | 0 | 3 | 2 | 0 | 0 | 0 | 0 | 2 | 3 |
| Nutsedge | 0 | 0 | 0 | 0 | 0 | 0 | 0 | 0 | — | 0 | 0 | — | — | — | — | 0 | 0 | — | 3 | 0 | 0 | 0 | 2 | 3 |
| Rape | 0 | 0 | 0 | 0 | 3 | 0 | 0 | 0 | 0 | 0 | 0 | 0 | 5 | 0 | 0 | 0 | 1 | 0 | 0 | 0 | 0 | 0 | 0 | 1 |
| Rice | 0 | 0 | 0 | 0 | 0 | 0 | 0 | 0 | 0 | 0 | 0 | 2 | 6 | 0 | 0 | 0 | 0 | 0 | 0 | 0 | 0 | 0 | 0 | 6 |
| Sorghum | 0 | 0 | 0 | 0 | 0 | 0 | 0 | 0 | 0 | 0 | 2 | 0 | 3 | 0 | 0 | 0 | 0 | 0 | 0 | 0 | 0 | 0 | 2 | 3 |
| Soybean | 0 | 0 | 0 | 0 | 0 | 0 | 0 | 0 | 0 | 0 | 3 | 0 | 6 | 0 | 0 | 0 | 4 | 0 | 2 | 0 | 0 | 0 | 0 | 10 |
| Sugar beet | 0 | 0 | 0 | 5 | 0 | 0 | — | 2 | 0 | 0 | 0 | 10 | 0 | 0 | 0 | 6 | 3 | 8 | 3 | 0 | 0 | 2 | 1 |
| Velvetleaf | 0 | 0 | 0 | 0 | 0 | 0 | 0 | 0 | 0 | 0 | 2 | 0 | 5 | 0 | 0 | 0 | 7 | 0 | 10 | 0 | 0 | 0 | 2 | 7 |

TABLE B-continued

| | | | | | | | | | | | | | | | | | | | | | | | |
|---|---|---|---|---|---|---|---|---|---|---|---|---|---|---|---|---|---|---|---|---|---|---|---|
| Wheat | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 6 |
| Wild buckwheat | 0 | 0 | 0 | 0 | 0 | 0 | 0 | 2 | 0 | 0 | 0 | 0 | 2 | 0 | 0 | 0 | 2 | 2 | 5 | 0 | 0 | 0 | 0 | 10 |
| Wild oat | 0 | 0 | 0 | 0 | 0 | 0 | 0 | 0 | 0 | 0 | 0 | 0 | 8 | 0 | 0 | 0 | 6 | 2 | 5 | 0 | 0 | 0 | 0 | 2 |

Test C

The compounds evaluated in this test were formulated in a non-phytoxic solvent mixture which include a surfactant and applied to the soil surface before plant seedlings emerged (preemergence application), to water that covered the soil surface (flood application), and to plants that were in the one-to-four leaf stage (postemergence application), A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgare*), bedstraw (*Galium aparine*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), giant foxtail (*Setaria faberii*), johnsongrass (*Sorghum halpense*), lambsquarters (*Chenopodium album*), morningglory (*pomoea hederacea*), pigweed (*Amaranthus retroflexus*), rape (*Brassica napus*), ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonurn convulvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*), barnyardgrass (*Echinochloa crus-galli*) and Late watergrass (*Echinocloa oryzicola*) grown to the 1 and 2 leaf stage for testing.

All plant species were grown using normal greenhouse practices. Visual evaluations of injury expressed on treated plants, when compared to untreated controls, were recorded approximately fourteen to twenty one days after application of the test compound. Plant response ratings, summarized in Table C, were recorded on a 0 to 100 scale where 0 is no effect and 100 is complete control. A dash (-) response means no test result.

TABLE C

| | COMPOUND 8 | | COMPOUND 8 |
|---|---|---|---|
| Rate 125 g/ha POSTEMERGENCE | | Rate 125 g/ha PREEMERGENCE | |
| Barley Igri | 45 | Barley Igri | 0 |
| Barnyard 2 | 40 | Barnyardgrass | 0 |
| Barnyardgrass | 45 | Bedstraw | 0 |
| Bedstraw | 95 | Blackgrass | 0 |
| Blackgrass | 45 | Chickweed | 35 |
| Chickweed | 95 | Cocklebur | 0 |
| Cocklebur | 100 | Corn | 0 |
| Corn | 40 | Cotton | 0 |
| Cotton | 100 | Crabgrass | 10 |
| Crabgrass | 65 | Downy Brome | 0 |
| Downy Brome | 70 | Giant foxtail | 20 |
| Duck salad | 0 | Italn. Rygrass | 10 |
| Giant foxtail | 80 | Johnsongrass | 0 |
| Italn. Rygrass | 65 | Lambsquarter | 70 |
| Johnsongrass | 70 | Morningglory | 0 |
| Lambsquarter | 100 | Rape | 0 |
| Morningglory | 100 | Redroot Pigweed | 70 |
| Rape | 90 | Soybean | 0 |
| Redroot Pigweed | 100 | Speedwell | 90 |
| Rice Japonica | 35 | Sugar beet | 0 |
| Soybean | 90 | Velvetleaf | 0 |
| Speedwell | 100 | Wheat | 0 |
| Sugar beet | 100 | Wild buckwheat | 80 |
| Umbrella sedge | 10 | Wild oat | 30 |
| Velvetleaf | 100 | | |
| Watergrass 2 | 25 | | |
| Wheat | 60 | | |
| Wild buckwheat | 100 | | |
| Wild oat | 35 | | |
| Rate 62 g/ha POSTEMERGENCE | | Rate 62 g/ha PREEMERGENCE | |
| Barley Igri | 40 | Barley Igri | 0 |
| Barnyard 2 | 40 | Barnyardgrass | 0 |
| Barnyardgrass | 35 | Bedstraw | 0 |
| Bedstraw | 95 | Blackgrass | 0 |
| Blackgrass | 45 | Chickweed | 35 |
| Chickweed | 95 | Cocklebur | 0 |
| Cocklebur | 100 | Corn | 0 |
| Corn | 30 | Cotton | 0 |
| Cotton | 100 | Crabgrass | 0 |
| Crabgrass | 50 | Downy Brome | 0 |
| Downy Brome | 70 | Giant foxtail | 0 |
| Duck salad | 0 | Italn. Rygrass | 10 |
| Giant foxtail | — | Johnsongrass | 0 |
| Italn. Rygrass | 45 | Lambsquarter | — |
| Johnsongrass | 70 | Morningglory | 0 |
| Lambsquarter | 95 | Rape | 0 |
| Morningglory | 100 | Redroot Pigweed | 0 |
| Rape | 90 | Soybean | 0 |
| Redroot Pigweed | 100 | Speedwell | 90 |
| Rice Japonica | 35 | Sugar beet | 0 |
| Soybean | 75 | Velvetleaf | 0 |
| Speedwell | 100 | Wheat | 0 |
| Sugar beet | 95 | Wild buckwheat | 30 |
| Umbrella sedge | 0 | Wild oat | 20 |
| Velvetleaf | 100 | | |
| Watergrass 2 | 20 | | |
| Wheat | 60 | | |
| Wild buckwheat | 100 | | |
| Wild Oat | 35 | | |
| Rate 31 g/ha POSTEMERGENCE | | Rate 31 g/ha PREEMERGENCE | |
| Barley Igri | 40 | Barley Igri | 0 |
| Barnyard 2 | 30 | Barnyardgrass | 0 |
| Barnyardgrass | 25 | Bedstraw | 0 |
| Bedstraw | 90 | Blackgrass | 0 |
| Blackgrass | 45 | Chickweed | 0 |
| Chickweed | 95 | Cocklebur | 0 |
| Cocklebur | 90 | Corn | 0 |
| Corn | 25 | Cotton | 0 |

TABLE C-continued

| | COMPOUND 8 | | COMPOUND 8 |
|---|---|---|---|
| Cotton | 100 | Crabgrass | 0 |
| Crabgrass | 50 | Downy Brome | 0 |
| Downy Brome | 70 | Giant foxtail | 0 |
| Duck salad | 0 | Italn. Rygrass | 0 |
| Giant foxtail | 70 | Johnsongrass | 0 |
| Italn. Rygrass | 45 | Lambsquarter | 50 |
| Johnsongrass | 70 | Morningglory | 0 |
| Lambsquarter | 95 | Rape | 0 |
| Morningglory | 100 | Redroot Pigweed | 0 |
| Rape | 80 | Soybean | 0 |
| Redroot Pigweed | 90 | Speedwell | 0 |
| Rice Japonica | 30 | Sugar beet | 0 |
| Soybean | 75 | Velvetleaf | 0 |
| Speedwell | 100 | Wheat | 0 |
| Sugar beet | 90 | Wild buckwheat | 10 |
| Umbrella sedge | 0 | Wild oat | 10 |
| Velvet leaf | 100 | | |
| Watergrass 2 | 20 | | |
| Wheat | 50 | | |
| Wild buckwheat | 100 | | |
| Wild oat | 35 | | |
| Rate 16 g/ha POSTEMERGENCE | | Rate 16 g/ha PREEMERGENCE | |
| Barley Igri | 35 | Barley Igri | 0 |
| Barnyard 2 | 30 | Barnyardgrass | 0 |
| Barnyardgrass | 20 | Bedstraw | 0 |
| Bedstraw | 80 | Blackgrass | 0 |
| Blackgrass | 40 | Chickweed | 0 |
| Chickweed | 90 | Cocklebur | 0 |
| Cocklebur | 90 | Corn | 0 |
| Corn | 25 | Cotton | 0 |
| Cotton | 100 | Crabgrass | 0 |
| Crabgrass | 40 | Downy Brome | 0 |
| Downy Brome | 70 | Giant foxtail | 0 |
| Duck salad | 0 | Italn. Rygrass | 0 |
| Giant foxtail | 50 | Johnsongrass | 0 |
| Italn. Rygrass | 45 | Lambsquarter | 50 |
| Johnsongrass | 40 | Morningglory | 0 |
| Lambsquarter | 90 | Rape | 0 |
| Morningglory | 95 | Redroot Pigweed | 0 |
| Rape | 50 | Soybean | 0 |
| Redroot Pigweed | 90 | Speedwell | 0 |
| Rice Japonica | 30 | Sugar beet | 0 |
| Soybean | — | Velvetleaf | 0 |
| Speedwell | 100 | Wheat | 0 |
| Sugar beet | 85 | Wild buckwheat | 10 |
| Umbrella sedge | 0 | Wild oat | 10 |
| Velvetleaf | 100 | | |
| Watergrass 2 | 0 | | |
| Wheat | 40 | | |
| Wild buckwheat | 90 | | |
| Wild oat | 35 | | |

Test D

Seeds, rhizomes, or plant parts of alexandergrass (*Brachiaria plantaginea*), alfalfa (*Medicago sativa*), annual bluegrass (*Poa annua*), bermudagrass (*Cynodon dactylon*), broadleaf signalgrass (*Brachiaria platyphylia*), common purslane (*Portulaca oleracea*), common ragweed (*Ambrosia artemisiifolia*), dallisgrass (*Paspalum dilatatum*), goosegrass (*Eleusine indica*), guineagrass (*Panicum maximum*), itchgrass (*Rottboellia cochinchinensis*), johnsongrass (*Sorghum halepense*), large crabgrass (*Digitaria sanguinalis*), P.J. legume (*Pueraria javanica*), peanut (*Arachis hypoagaea*), pitted morningglory (*Ipomoea lacunosa*), purple nutsedge (*Cyperus rotundus*), sandbur (*Southern sandbur*), smooth crabgrass (*Digitaria ischaemum*), sourgrass (*Panicum Texanum*) and yellow nutsedge (*Cyperus esculentus*) were planted into greenhouse pots containing greenhouse planting medium. Each pot contained only one plant species.

The test compound was formulated in a non-phytotoxic solvent mixture which includes a surfactant and applied preemergence and/or postemergence to the plants. Preemergence applications were made within one day of planting the seeds or plant pans. Postemergence applications were applied when the plants were in the two to four leaf stage (three to twenty cm). Untreated control plants and treated plants were placed in the greenhouse and visually evaluated for injury at 14 to 28 days after herbicide application. Plant response ratings, summarized in Table D, are based on a 0 to 100 scale where 0 is no injury and 100 is complete control. A dash (-) response indicates no test result.

TABLE D

| | COMPOUND | | | COMPOUND | |
|---|---|---|---|---|---|
| Rate 0250 g/ha | 1 | 18 | Rate 0250 g/ha | 1 | 18 |
| POSTEMERGENCE | | | PREEMERGENCE | | |
| Alexandergrass | — | 50 | Alexandergrass | — | 100 |
| Alfalfa Var. | 0 | 85 | Alfalfa Var. | 0 | 30 |
| Ann Bluegrass | 0 | — | Ann Bluegrass | 0 | — |
| Bermudagrass | — | 70 | Bermudagrass | 0 | 98 |
| Brdlf Sgnlgrass | 0 | 30 | Brdlf Sgnlgrass | 0 | 85 |
| Cmn Purslane | 100 | 100 | Cmn Purslane | — | 100 |
| Cmn Ragweed | 0 | 100 | Cmn Ragweed | 0 | 100 |
| Dallisgrass | 0 | 80 | Dallisgrass | 0 | 100 |
| Goosegrass | 0 | 40 | Goosegrass | 0 | 100 |
| Guineagrass | 0 | — | Guineagrass | 0 | 100 |
| Itchgrass | 0 | 30 | Itchgrass | 0 | 98 |
| Johnson grass | 0 | 25 | Johnson grass | 0 | 70 |
| Large Crabgrass | 0 | 25 | Large Crabgrass | 0 | 100 |
| P J Legume | 0 | — | P J Legume | 0 | — |
| Peanuts | 60 | 75 | Peanuts | 0 | 0 |
| Pit Morninglory | 0 | — | Pit Morninglory | 0 | 98 |
| Purple Nutsedge | 0 | 10 | Purple Nutsedge | — | 100 |
| Sandbur | — | 30 | Sandbur | 0 | 100 |
| Smooth Crabgras | 0 | — | Smooth Crabgras | 0 | — |
| Sourgrass | — | 90 | Sourgrass | — | 100 |
| Texas Panicum | 10 | 98 | Texas Panicum | 0 | 98 |
| Yellow Nutsedge | 0 | — | Yellow Nutsedge | 0 | — |

Test E

Plant species in the preemergence tests consisted of barnyardgrass (*Echinochloa crus-galli*), bedstraw (*Galium aparine*), bluegrass (*Poa trivialis*), cassia (*Cassia tora*), cheat grass (*Bromus secalinus*), cocklebur (*Xanthium pensylvanicum*), corn (*Zea mays*), crabgrass (*Digitaria sanguinalis*), curly indigo (*Aeschynomene virginica*), giant foxtail (*Setaria faberii*), jimsonweed (*Datura stramonium*), johnsongrass (*Sorghum halpense*), morningglory (*Ipomoea hederacea*), mustard (*Sinapis arvensis*), nutsedge (*Cyperus rotundus*), pig weed (*Amaranthus retroflexus*), rice (*Oryza sativa*), sorghum (*Sorghum bicolor*), soybean (*Glycine max*), sugar beet (*Beta vulgaris*), teaweed (*Sida Spinosa*), velvetleaf (*Abutilon theophrasti*), wheat (*Triticum aestivum*) and wild oat (*Avena fatua*). All plant species were planted one day before application of the compound. Compounds evaluated in this test were formulated in a non-phytotoxic solvent mixture which includes a surfactant and applied to the soil surface before plant seedlings emerged (preemergence application).

All plant species were grown using normal greenhouse practices. Visual evaluations of injury expressed on treated plants, when compared to untreated controls, were recorded approximately fourteen to twenty one days after application of the test compound. Plant response ratings, summarized in Table E, were recorded on a 0 to 10 scale where 0 is no effect and 10 is complete control. A dash (-) response means no test result.

TABLE E

| Rate 500 g/h | COM-POUND 1 | Rate 120 g/h | COM-POUND 1 |
|---|---|---|---|
| PREEMERGENCE | | PREEMERGENCE | |
| Barnyardgrass | 2 | Barnyardgrass | 0 |
| Bluegrass | 8 | Bluegrass | 0 |
| Cassia | 0 | Cassia | 0 |
| Cheatgrass | 0 | Cheatgrass | 0 |
| Cocklebur | 0 | Cocklebur | 0 |
| Corn | 0 | Corn | 0 |
| Crabgrass | 8 | Crabgrass | 0 |
| Curly Indigo | 8 | Curly Indigo | 0 |
| Giant foxtail | 4 | Giant foxtail | 0 |
| Jimsonweed | 3 | Jimsonweed | 0 |
| Johnsongrass | 4 | Johnsongrass | 0 |
| Morningglory | 0 | Morningglory | 0 |
| Mustard | 3 | Mustard | 0 |
| Nutsedge | 0 | Nutsedge | 0 |
| Pig weed | 0 | Pig weed | 0 |
| Rice | 0 | Rice | 0 |
| Sorghum | 2 | Sorghum | 0 |
| Soybean | 0 | Soybean | 0 |
| Sugar beet | 0 | Sugar beet | 0 |
| Teaweed | 10 | Teaweed | 0 |
| Velvetleaf | 7 | Velvetleaf | 0 |
| Wheat | 0 | Wheat | 0 |
| Wild Oat | 0 | Wild Oat | 0 |

Test F

The compounds evaluated in this test were formulated in a non-phytotoxic solvent mixture which includes a surfactant and applied to plants that were in the one-to-four leaf stage (postemergence application).

Plant species in the postemergence tests consisted of alfalfa (*Medicago saliva*), barnyardgrass (*Echinochloa crusgalli*), cassia (*Cassia tora*), cocklebur (*Xanthium pensylvanicum*), coffee weed (*Daubentonia texana pierce*), corn (*Zea mays*), cotton (*Gossypium hirsutum*), crabgrass (*Digitaria sanguinalis*), giant foxtail (*Setaria faberii*), jimsonweed (*Datura stramonium*), morningglory (*Ipomoea hederacea*), nutsedge (*Cyperus rotundus*), rice (*Oryza saliva*), sorghum (*Sorghum bicolor*), soybean (*Glycine max*), velvetleaf (*Abutilon theophrasti*), wheat (*Triticum aestivum*) and wild oat (*Avena fatua*).

All plant species were grown using normal greenhouse practices. Visual evaluations of injury expressed on treated plants, when compared to untreated controls, were recorded approximately fourteen to twenty one days after application of the test compound. Plant response ratings, summarized in Table F, were recorded on a 0 to 10 scale where 0 is no effect and 10 is complete control. A dash (-) response means no test result.

TABLE F

| 500 g/ha | COM-POUND 1 | 3 | 125 g/ha | COM-POUND 1 | 3 |
|---|---|---|---|---|---|
| POSTEMERGENCE | | | POSTEMERGENCE | | |
| Alfalfa | 5 | 4 | Alfalfa | 3 | 4 |
| Barnyardgrass | 4 | 4 | Barnyardgrass | 3 | 4 |
| Cassia | 6 | 8 | Cassia | 4 | 2 |
| Cocklebur | 6 | 6 | Cocklebur | 2 | 4 |
| Coffee weed | 8 | 8 | Coffee weed | 6 | 4 |
| Corn | 3 | 4 | Corn | 3 | 2 |
| Cotton | 10 | 10 | Cotton | 8 | 9 |
| Crabgrass | 3 | 7 | Crabgrass | 2 | 3 |
| Giant Foxtail | 7 | 6 | Giant Foxtail | 3 | 3 |
| Jimsonweed | 10 | 10 | Jimsonweed | 10 | 10 |
| Morninglory | 6 | 7 | Morninglory | 7 | 4 |
| Nutsedge | 2 | 3 | Nutsedge | 0 | 0 |
| Rice | 2 | — | Rice | 0 | 0 |
| Sorghum | 5 | 9 | Sorghum | 3 | 3 |
| Soybean | 9 | 7 | Soybean | 6 | 6 |
| Velvetleaf | 9 | 10 | Velvetleaf | 9 | 10 |
| Wheat | 3 | 4 | Wheat | 2 | 2 |
| Wild Oats | 4 | 3 | Wild Oats | 2 | 2 |

Test G

Compounds were evaluated under various conditions for their effectiveness in controlling the growth of nutsedge (*Cyperus rotundus*) in this test. The test compound was applied in a non-phytotoxic solvent (generally water) to nutsedge tubers which had been previously seeded into pots containing a sandy loam soil and allowed to grow for several weeks, these were treated as the post-emergence treatment. Additionally, freshly prepared pots were seeded with tubers. These treatments constituted the preemergence treatment where the covering soil was treated with the compound. In another treatment, the exposed tubers were allowed to contact the sprayed test compound directly. In the final treatment, the soil used to cover the tubers was placed in a bag and treated with the appropriate amount of the test compound. The contents of the bag were then mixed (incorporated) and placed on the surface of the seeded pots. All treatments were maintained in the greenhouse where visual ratings were made at two and four weeks after application of the test compound. Plant response ratings, summarized in Table G, were recorded on a 0 to 10 scale where 0 is no effect and 10 is complete control. A dash (-) response means no test result.

TABLE G

| Rate 2 g/h | COM-POUND 1 | Rate 2 g/h | COM-POUND 1 |
|---|---|---|---|
| Direct Tuber Spray | 2 weeks | Direct Tuber Spray | 4 weeks |
| Nutsedge | 0 | Nutsedge | 2 |

Test H

This test evaluated the effects of test compounds on monocot weeds grown in association with cereal crops such as rice, wheat or barley. In the current test, compounds were applied to the foliage of barnyardgrass (*Echinochloa crusgalli*) and Japonica rice (*Oriza sativa*) or to the surface of pots recently seeded with the test species. All test compounds were first formulated in a non-phytotoxic solvent mixture which includes a surfactant and sprayed over the foliage or soil surface to the test unit. After application of the test compound, the plants were maintained in the greenhouse under standard conditions until such time as they were visually evaluated. Plant response ratings, summarized in Table H, were recorded on a 0 to 10 scale where 0 is no effect and 10 is complete control. A dash (-) response means no test result.

TABLE H

| | COMPOUND 2 | | COMPOUND 1 |
|---|---|---|---|
| Rate 2000 g/h | | Rate 500 g/h | |
| PREEMERGENCE | | POSTEMERGENCE | |
| Barnyardgrass | 6 | Barnyardgrass | 7 |
| Japonica Rice | 0 | Japonica Rice | 2 |
| Rice | 0 | Rice | — |

| | COMPOUND 1 | COMPOUND 2 | COMPOUND 1 |
|---|---|---|---|
| Rate 500 g/h | | | Rate 250 g/h |
| PREEMERGENCE | | | POSTEMERGENCE |
| Barnyardgrass | 3 | 0 | Barnyardgrass | 0 |
| Japonica Rice | 0 | 0 | Japonica Rice | 4 |
| Rice | 0 | 0 | Rice | 0 |

| | COMPOUND 1 | | COMPOUND 1 |
|---|---|---|---|
| Rate 250 g/h | | Rate 125 g/h | |
| PREEMERGENCE | | POSTEMERGENCE | |
| Barnyardgrass | 2 | Barnyardgrass | 0 |
| Japonica Rice | 0 | Japonica Rice | 0 |
| Rice | 0 | Rice | 0 |

| | COMPOUND 1 |
|---|---|
| Rate 125 g/h | |
| PREEMERGENCE | |
| Barnyardgrass | 0 |
| Japonica Rice | 0 |
| Rice | 0 |

We claim:

1. A compound of Formula I or II, or an agriculturally-suitable salt thereof,

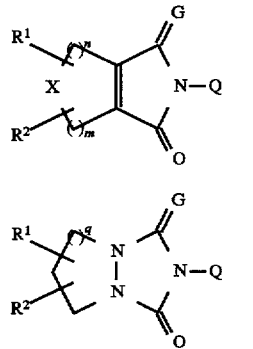

wherein
G is O; S; NH; $N(C_1-C_4$ alkyl); or $N(C_1-C_4$ haloalkyl);
$R^1$ is hydrogen; halogen; hydroxy; SH; $C_1-C_3$ alkoxy; $C_1-C_3$ haloalkoxy; $C_1-C_3$ alkylthio; $C_1-C_3$ haloalkylthio; $C_2-C_4$ alkylcarbonyloxy; or $C_2-C_4$ haloalkylcarbonyloxy;

$R^2$ is hydrogen; hydroxy; or halogen; or when $R^1$ and $R^2$ are bonded to the same carbon atom they can be taken together with the carbon to which they are attached to form C=O; or when $R^1$ and $R^2$ are bonded to adjacent atoms they can be taken together with the carbons to which they are attached to form

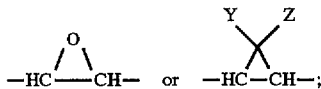

Y and Z are each independently H; halogen; $C_1-C_2$ alkyl; or $C_1-C_2$ haloalkyl; n and m are each independently 0; 1; 2; or 3; provided that m+n is 2 or 3; q is 1 or 2;

X is $CH_2$; CH(halogen); $CF_2$; $CHOCH_2F$; $CHOCF_3$; $CHOCH_2CF_3$; O; $S(O)_{0-2}$; NH; $N(C_1-C_4$ alkyl); or $N(C_1-C_4$ haloalkyl);

Q is selected from the group

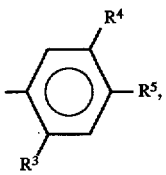
Q-1

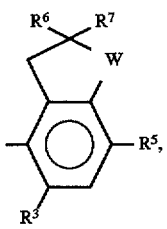
Q-2

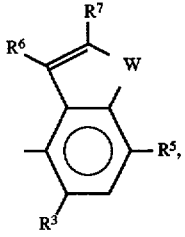
Q-3

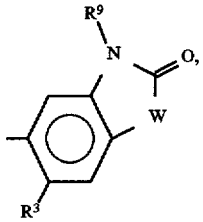
Q-4

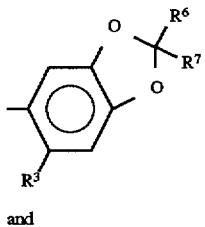
Q-5 and

-continued

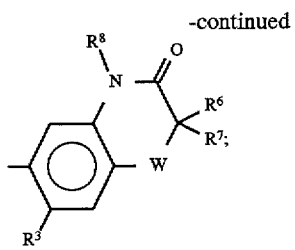

Q-6

W is O or S;

R³ is chlorine or fluorine;

R⁴ is; $C_1$–$C_8$ alkyl; $C_1$–$C_8$ haloalkyl; halogen; OH; OR⁹; SH; S(O)$_p$R⁹; COR⁹; CO$_2$R⁹; C(O)SR⁹; C(O)NR¹¹R¹²; CHO; CR¹¹=NOR¹⁸; CH=CR¹⁹CO$_2$R⁹; CH$_2$CHR¹⁹CO$_2$R⁹; CO$_2$N=CR¹³R¹⁴; NO$_2$; CN; NHSO$_2$R¹⁵; NHSO$_2$NHR¹⁵; NR⁹R²⁰; NH$_2$ or phenyl optionally substituted with at least one member independently selected from $C_1$–$C_4$ alkyl;

p is 0; 1; or 2;

R⁵ is $C_1$–$C_2$ alkyl; $C_1$–$C_2$ haloalkyl; OCH$_3$; SCH$_3$; OCHF$_2$; halogen; CN or NO$_2$;

R⁶ is H; $C_1$–$C_3$ alkyl; $C_1$–$C_3$ haloalkyl; or halogen;

R⁷ is H; $C_1$–$C_3$ alkyl; halogen; $C_1$–$C_3$ haloalkyl; cyclopropyl; vinyl; $C_2$ alkynyl; CN; C(O)R²⁰; CO$_2$R²⁰; C(O)NR²⁰R²¹; CR¹⁶R¹⁷CN; CR¹⁶R¹⁷C(O)R²⁰; CR¹⁶R¹⁷CO$_2$R²⁰; CR¹⁶R¹⁷C(O)NR²⁰R²¹; CHR¹⁶OH; CHR¹⁶OC(O)R²⁰; OCHR¹⁶OC(O)NR²⁰R²¹; or Q is Q-2 and R⁶ and R⁷ are taken together with the carbon to which they are attached to form C=O;

R⁸ is $C_1$–$C_6$ alkyl; $C_1$–$C_6$ haloalkyl; $C_2$–$C_6$ alkoxyalkyl; $C_3$–$C_6$ alkenyl; or $C_3$–$C_6$ alkynyl; , R⁹ is $C_1$–$C_8$ alkyl; $C_3$–$C_8$ cycloalkyl; $C_3$–$C_8$ alkenyl; $C_3$–$C_8$ alkynyl; $C_1$–$C_8$haloalkyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_1$–$C_8$ alkylsulfonyl; phenylsulfonyl optionally substituted on the phenyl ring with at least one substituent selected from the group halogen and $C_1$–$C_4$ alkyl; $C_4$–$C_8$ alkoxyalkoxyalkyl; $C_4$–$C_8$cycloalkylalkyl; $C_4$–$C_8$ alkenoxyalkyl; $C_4$–$C_8$ alkynoxyalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; $C_4$–$C_8$ haloalkenoxyalkyl; $C_4$–$C_8$ haloalkynoxyalkyl; $C_6$–$C_8$cycloalkylthioalkyl; $C_4$–$C_8$ alkenylthioalkyl; $C_4$–$C_8$ alkynylthioalkyl; $C_1$–$C_4$alkyl substituted with phenoxy or benzyloxy, each ring optionally substituted with at least one substituent selected from the group halogen, $C_1$–$C_3$ alkyl and $C_1$–$C_3$ haloalkyl; $C_4$–$C_8$ trialkylsilylalkyl; $C_3$–$C_8$ cyanoalkyl; $C_3$–$C_8$ halocycloalkyl; $C_3$–$C_8$ haloalkenyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $C_2$–$C_8$ alkylcarbonyl; benzyl optionally substituted with at least one substituent selected from the group halogen, $C_1$–$C_3$ alkyl and $C_1$–$C_3$ haloalkyl; CHR¹⁶COR¹⁰; CHR¹⁶CO$_2$R¹⁰; CHR¹⁶P(O)(OR¹⁰)$_2$; CHR¹⁶P(S)(OR¹⁰)$_2$; CHR¹⁶C(O)NR¹¹R¹²; or CHR¹⁶C(O)NH$_2$;

R¹⁰ is $C_1$–$C_6$ alkyl; $C_2$–$C_6$ alkenyl; or $C_2$–$C_6$ alkynyl;

R¹¹ and R¹³ are independently hydrogen or $C_1$–$C_4$ alkyl;

R¹² and R¹⁴ are independently $C_1$–$C_4$ alkyl or phenyl optionally substituted with at least one substituent selected from the group halogen, $C_1$–$C_3$ alkyl and –$C_1$–$C_3$ haloalkyl; or R¹¹ and R¹² are taken together to form —(CH$_2$)$_5$—, —(CH$_2$)$_4$— or —CH$_2$CH$_2$OCH$_2$CH$_2$—, each ring thus formed optionally substituted with a substituent selected from the group $C_1$–$C_3$ alkyl, phenyl and benzyl; or R¹³ and R¹⁴ are taken together with the carbon to which they are attached to form $C_3$–$C_8$ cycloalkyl;

R¹⁵ is $C_1$–$C_4$ alkyl or $C_1$–$C_4$ haloalkyl;

R¹⁶ and R¹⁷ are independently H or $C_1$–$C_4$ alkyl;

R¹⁸ is H, $C_1$–$C_6$ alkyl, $C_3$–$C_6$ alkenyl or $C_3$–$C_6$ alkynyl;

R¹⁹ is H, $C_1$–$C_4$ alkyl or halogen;

R²⁰ is H; $C_1$–$C_6$ alkyl; $C_3$–$C_6$ cycloalkyl; $C_3$–$C_6$ alkenyl; $C_3$–$C_6$ alkynyl; $C_2$–$C_6$ alkoxyalkyl; $C_1$–$C_6$ haloalkyl; phenyl optionally substituted with at least one substituent selected from the group halogen, $C_1$–$C_4$ alkyl, and $C_1$–$C_4$ alkoxy; —CH$_2$CO$_2$($C_1$–$C_4$ alkyl); or —CH(CH$_3$) CO$_2$($C_1$–$C_4$ alkyl); and R²¹ is H; $C_1$–$C_2$ alkyl; or C(O)O($C_1$–$C_4$ alkyl); provided that (i) R¹ is other than hydrogen in compounds of Formula I when X is CH$_2$ and R² is hydrogen; and (ii) R² is other than hydrogen or hydroxy in compounds of Formula II when Q is Q-1, Q-2, Q-4, or Q-6 and q is 2.

2. A compound of claim 1 wherein:

G is O;

R¹ is hydrogen or halogen;

R² is halogen;

Q is Q-1, Q-2 or Q-6;

R⁵ is $C_1$–$C_2$ haloalkyl; OCH$_3$; OCHF$_2$; CN; NO$_2$; or halogen;

R⁶ is hydrogen; $C_1$–$C_3$ alkyl; $C_2$–$C_3$ alkynyl; $C_2$–$C_3$ haloalkynyl; or halogen;

R⁷ is H; and

W is O.

3. A compound of claim 2 wherein:

R⁴ is halogen; OR⁹; S(O)$_p$R⁹; COR⁹; CO$_2$R⁹; C(O)NR¹¹R¹²; CH=CHCO$_2$R⁹; NHSO$_2$R¹⁵ or NHSO$_2$NHR¹⁵;

R⁵ is halogen;

R⁶ is hydrogen or $C_1$–$C_3$ alkyl; and

R⁹ is $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_1$–$C_4$ alkyl substituted with phenoxy or benzyloxy, each ring optionally substituted with at least one substituent selected from the group halogen, $C_1$–$C_3$ alkyl and $C_1$–$C_3$ haloalkyl; $C_3$–$C_8$ haloalkenyl; $C_3$–$C_8$ haloalkynyl; $C_2$–$C_8$ alkyl carbonyl; benzyl optionally substituted with at least one substituent selected from the group halogen, $C_1$–$C_3$ alkyl and $C_1$–$C_3$ haloalkyl; CHR¹⁶COR¹⁰; CHRI¹⁶CO$_2$R¹⁰; CHR¹⁶P(O)(OR¹⁰)$_2$; CHR¹⁶C(O)NR¹¹R¹²; or CHR¹⁶C(O)NH$_2$.

4. A compound of claim 3 wherein

R¹ is hydrogen or fluorine;

R² is fluorine;

X is CH$_2$ or O;

R⁵ is chlorine or fluorine; and

R⁹ is $C_1$–$C_6$ alkyl; $C_3$–$C_6$ alkenyl; $C_3$–$C_6$ alkynyl; $C_1$–$C_6$ haloalkyl; $C_2$–$C_8$alkoxyalkyl; CH$_2$ substituted with phenoxy or benzyloxy, each ring optionally substituted with at least one substituent selected from the group halogen, $C_1$–$C_3$ alkyl and $C_1$–$C_3$ haloalkyl; $C_3$–$C_8$ haloalkenyl; $C_2$–$C_8$ alkyl carbonyl; benzyl optionally substituted with at least one substituent selected from the group halogen, $C_1$–$C_3$ alkyl and $C_1$–$C_3$ haloalkyl; $CHR^{16}COR^{10}$; $CHR^{16}CO_2R^{10}$; or $CHR^{16}P(O)(OR^{10})_2$.

5. A compound of claim 4 which is selected from the group:

2-[4-chloro-2-fluoro-5-(2-propynyloxy)phenyl]-6-fluorotetrahydro-1H-[1,2,4]triazol[1,2-α]pyridazine-1,3(2H)-dione;

2-[4-chloro-2-fluoro-5-(2-propynyloxy)phenyl]-6-fluorodihydro-1H,5H-pyrazole[1,2-α]triazole-1,3(2H)-dione;

2-[4-chloro-2-fluoro-5-(2-propynyloxy)phenyl]-5-fluoro-4,5,6,7-tetrahydro-1H-isoindole-,1,3(2H)-dione; and 2-[4-chloro-2-fluoro-5-(2-propynyloxy)phenyl]-6,7-dihydropyrano[3,4-c]-pyrrole-1,3(2H,4H)-dione.

6. A herbicidal composition comprising an effective mount of a compound of claim 1 and at least one component selected from surfactants, solid diluents and liquid diluents.

7. A method for controlling growth of undesired vegetation comprising applying to the locus to be protected an effective mount of a compound of claim 1.

8. A method for controlling weeds in plantation crops comprising applying to the locus of a plantation crop an effective mount of a compound of claim 1.

9. A method for controlling weeds in plantation crops comprising applying to the locus of a plantation crop an effective mount of a composition of claim 6.

* * * * *